(12) United States Patent
Wang et al.

(10) Patent No.: US 11,643,463 B2
(45) Date of Patent: *May 9, 2023

(54) MONOCLONAL ANTIBODIES TO CYTOTOXIC T-LYMPHOCYTE-ASSOCIATED PROTEIN 4 (CTLA-4)

(71) Applicant: WUXI Biologics (Shanghai) Co., Ltd., Shanghai (CN)

(72) Inventors: Zhuozhi Wang, Shanghai (CN); Jing Li, Lexington, MA (US); Gennady Gololobov, Gaithersburg, MD (US); Jianqing Xu, Shanghai (CN)

(73) Assignee: WUXI Biologics (Shanghai) Co., Ltd., Shanghai (CN)

( * ) Notice: Subject to any disclaimer, the term of this patent is extended or adjusted under 35 U.S.C. 154(b) by 56 days.

This patent is subject to a terminal disclaimer.

(21) Appl. No.: 16/614,777

(22) PCT Filed: May 19, 2017

(86) PCT No.: PCT/CN2017/085134
§ 371 (c)(1),
(2) Date: Nov. 18, 2019

(87) PCT Pub. No.: WO2018/209701
PCT Pub. Date: Nov. 22, 2018

(65) Prior Publication Data
US 2020/0277377 A1    Sep. 3, 2020

(51) Int. Cl.
C07K 16/46 (2006.01)
C07K 16/00 (2006.01)
C07K 16/28 (2006.01)
C12N 15/63 (2006.01)
A61K 39/00 (2006.01)

(52) U.S. Cl.
CPC .......... *C07K 16/2818* (2013.01); *C12N 15/63* (2013.01); *A61K 2039/505* (2013.01); *C07K 2317/24* (2013.01); *C07K 2317/34* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,859,205 A * | 1/1999 | Adair | C07K 16/465 530/387.3 |
| 6,051,227 A | 4/2000 | Allison et al. | |
| 7,452,535 B2 | 11/2008 | Davis et al. | |
| 7,465,446 B2 | 12/2008 | Lowy et al. | |
| 7,744,875 B2 | 6/2010 | Lowy et al. | |
| 8,475,790 B2 | 7/2013 | Jure-Kunkel et al. | |
| 8,518,404 B2 | 8/2013 | Daugherty et al. | |
| 8,993,524 B2 | 3/2015 | Bedi et al. | |
| 9,562,073 B2 | 2/2017 | Moore et al. | |
| 9,944,689 B2 | 4/2018 | Wang et al. | |
| 10,167,337 B2 | 1/2019 | Allison et al. | |
| 10,174,113 B2 | 1/2019 | Yang et al. | |
| 10,196,445 B1 | 2/2019 | Engelhardt et al. | |
| 10,463,686 B2 | 11/2019 | Agrawal et al. | |
| 10,842,743 B2 | 11/2020 | Roth et al. | |
| 10,842,763 B2 | 11/2020 | Slusher et al. | |
| 10,869,926 B2 | 12/2020 | Zhou et al. | |
| 11,078,281 B2 * | 8/2021 | Wang | C12N 15/63 |
| 2015/0104409 A1 | 4/2015 | Hanson et al. | |
| 2016/0145355 A1 * | 5/2016 | Saha | C07K 16/2818 424/136.1 |
| 2016/0347848 A1 | 12/2016 | Hammond et al. | |
| 2019/0055321 A1 | 2/2019 | Krystek et al. | |
| 2019/0076452 A1 | 3/2019 | Rios-Doria et al. | |
| 2019/0241660 A1 | 8/2019 | Giroir et al. | |
| 2019/0241662 A1 | 8/2019 | Luo et al. | |

(Continued)

FOREIGN PATENT DOCUMENTS

| | | |
|---|---|---|
| EP | 2734232 B1 | 11/2017 |
| WO | WO 2001014424 A2 | 3/2001 |

(Continued)

OTHER PUBLICATIONS

Edwards et al., The remarkable flexibility of the human antibody repertoire; isolation of over one thousand different antibodies to a single protein, BLyS. J Mol Biol. Nov. 14, 2003;334(1): 103-18. (Year: 2003).*

Lloyd et al., Modelling the human immune response: performance of a 1011 human antibody repertoire against a broad panel of therapeutically relevant antigens. Protein Eng Des Sel. Mar. 2009;22(3):159-68. (Year: 2009).*

Goel et al., Plasticity within the antigen-combining site may manifest as molecular mimicry in the humoral immune response. J Immunol. Dec. 15, 2004; 173(12):7358-67. (Year: 2004).*

Kanyavuz et al., Breaking the law: unconventional strategies for antibody diversification. Nat Rev Immunol. Jun. 2019; 19(6):355-368. (Year: 2019).*

(Continued)

*Primary Examiner* — Maher M Haddad
(74) *Attorney, Agent, or Firm* — Proskauer Rose, LLP; Fangli Chen

(57) ABSTRACT

The present invention provides CTLA-4 monoclonal antibodies, particularly humanized monoclonal antibodies specifically binding to CTLA-4 with high affinity. The present invention also provides functional monoclonal antibodies cross-reactive to CTLA-4 of human, cynomolgus monkey and mouse. The present invention further provides amino acid sequences of the antibodies of the invention, cloning or expression vectors, host cells and methods for expressing or isolating the antibodies. The epitopes of the antibodies are identified. Therapeutic compositions comprising the antibodies of the invention are also provided. The invention also provides methods for treating cancers and other diseases with anti-CTLA-4 antibodies.

4 Claims, 24 Drawing Sheets

Specification includes a Sequence Listing.

(56) References Cited

U.S. PATENT DOCUMENTS

| | | |
|---|---|---|
| 2019/0292599 A1 | 9/2019 | Liu et al. |
| 2019/0300606 A1 | 10/2019 | Woods et al. |
| 2019/0300967 A1 | 10/2019 | Bachireddy et al. |
| 2019/0352398 A1 | 11/2019 | Allison et al. |
| 2019/0359714 A1 | 11/2019 | Tipton et al. |
| 2019/0382490 A1 | 12/2019 | Loffredo et al. |
| 2020/0055937 A1 | 2/2020 | Calzone et al. |
| 2020/0148771 A1 | 5/2020 | Baeuerle et al. |
| 2020/0206346 A1 | 7/2020 | Li et al. |
| 2020/0255524 A1 | 8/2020 | Bonivi et al. |
| 2020/0405890 A1 | 12/2020 | Vasiljeva et al. |
| 2021/0023151 A1 | 1/2021 | Deng et al. |
| 2021/0032344 A1 | 2/2021 | Bhagavatheeswaran et al. |
| 2021/0040177 A1 | 2/2021 | Roberts et al. |
| 2021/0047410 A1 | 2/2021 | Liu et al. |

FOREIGN PATENT DOCUMENTS

| | | |
|---|---|---|
| WO | WO 2006101692 A1 | 9/2006 |
| WO | WO 2012120125 A1 | 9/2012 |
| WO | WO 2016/130986 A1 | 8/2016 |
| WO | 2016196237 A1 | 12/2016 |
| WO | WO 2017157964 A1 | 9/2017 |
| WO | WO 2018222711 A2 | 6/2018 |
| WO | WO 2018148555 A1 | 8/2018 |
| WO | WO 2018156802 A1 | 8/2018 |
| WO | WO 2019018841 A2 | 1/2019 |
| WO | WO 2019094352 A1 | 5/2019 |
| WO | WO 2019183036 A1 | 9/2019 |
| WO | WO 2019243471 A1 | 12/2019 |
| WO | WO 2020007368 A1 | 1/2020 |
| WO | WO 2020024932 A1 | 2/2020 |
| WO | WO 2020061526 A1 | 3/2020 |
| WO | WO 2000037504 | 6/2020 |
| WO | WO 2020214748 A1 | 10/2020 |
| WO | WO 2020252349 A1 | 12/2020 |
| WO | WO 2020252358 A1 | 12/2020 |
| WO | WO 2021062323 A1 | 4/2021 |
| WO | WO 2021064188 A1 | 4/2021 |

OTHER PUBLICATIONS

Kirkwood et al., "Phase II trial of tremelimumab (CP-675,206) in patients with advanced refractory or relapsed melanoma," Clin Cancer Res 16(3): 1042-1048 (2010). (Year: 2010).*
Prieto et al., "CTLA-4 blockade with ipilimumab: long-term follow-up of 177 patients with metastatic melanoma," Clin Cancer Res 18(7):2039-2047 (2012). (Year: 2012).*
Vandenborre et al. Interaction of CTLA-4 (CD152) with CD80 or CD86 inhibits human T-cell activation. Immunology. Nov. 1999;98(3):413-21. (Year: 1999).*
Eduardo Padlan, Anatomy of the antibody molecule. Mol Immunol. Feb. 1994;31(3):169-217. (Year: 1994).*
Paul, Fundamental Immunology, 3rd Edition, 1993, pp. 292-295. (Year: 1993).*
Rudikoff et al Single amino acid substitution altering antigen-binding specificity. Proc Natl Acad Sci U S A. Mar. 1982;79(6):1979-83. (Year: 1982).*
Portolano et al., Lack of promiscuity in autoantigen-specific H and L chain combinations as revealed by human H and L chain "roulette". J Immunol. Feb. 1, 1993;150(3):880-7. (Year: 1993).*
Brown et al. Tolerance of single, but not multiple, amino acid replacements in antibody VH CDR2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*
Padlan EA, Silverton EW, Sheriff S, Cohen GH, Smith-Gill SJ, Davies DR. Structure of an antibody-antigen complex: crystal structure of the HyHEL-10 Fab-lysozyme complex. PNAS. 1989;86:5938. (Year: 1989).*
MacCallum et al. Antibody-antigen interactions: contact analysis and binding site topography. J. Mol. Biol., 262, 732-745, 1996. (Year: 1996).*
Casset et al. A peptide mimetic of an anti-CD4 monoclonal antibody by rational design. Biochemical and Biophysical Research Communications, 307:198-205, 2003. (Year: 2003).*
Queen et al., A humanized antibody that binds to the interleukin 2 receptor. PNAS (1988):10029-10033. (Year: 1988).*
Riechmann et al., Reshaping human antibodies for therapy. Nature (1988) 332-327. (Year: 1988).*
Simmons, Andrew D et al. "Local secretion of anti-CTLA-4 enhances the therapeutic efficacy of a cancer immunotherapy with reduced evidence of systemic autoimmunity." Cancer immunology, immunotherapy : CII vol. 57,8 (2008): 1263-70. doi:10.1007/s00262-008-0451-3.
Ng Tang, Derek et al. "Increased frequency of $ICOS_+$ CD4 T cells as a pharmacodynamic biomarker for anti-CTLA-4 therapy." Cancer immunology research vol. 1,4 (2013): 229-34. doi:10.1158/2326-6066.CIR-13-0020.
Carbonnel, Franck et al. "Inflammatory bowel disease and cancer response due to anti-CTLA-4: is it in the flora?." Seminars in immunopathology vol. 39,3 (2017): 327-331. doi:10.1007/s00281-016-0613-x.
Sun, Jingjing et al. "Concurrent decrease in IL-10 with development of immune-related adverse events in a patient treated with anti-CTLA-4 therapy." Cancer immunity vol. 8 9. May 27, 2008.
Bakacs, Tibor, and Jitendra N Mehrishi. "Anti-CTLA-4 therapy may have mechanisms similar to those occurring in inherited human CTLA4 haploinsufficiency." Immunobiology vol. 220,5 (2015): 624-5. doi:10.1016/j.imbio.2014.11.019.
International Search Report and Written Opinion for PCT/CN2017/085134, dated Feb. 23, 2018.

* cited by examiner

W3162-1.145.10xAb.IgG1

W3162-1.154.8xAb.IgG1

W316.hBMK1.IgG1(ipilimumab)

SEQUENCE LISTING

<160> NUMBER OF SEQ ID NOS: 48

<210> SEQ ID NO 1
<211> LENGTH: 114

```
<212> TYPE: PRT
<213> ORGANISM: Artificial Sequence
<220> FEATURE:
<223> OTHER INFORMATION: Synthetic Construct

<400> SEQUENCE: 1

Glu Glu Gln Leu Val Glu Ser Gly Gly Gly Leu Val Gln Pro Gly Lys
1               5                   10                  15

Ser Leu Lys Leu Ser Cys Ser Ala Ser Gly Phe Thr Phe Arg Ser Ser
            20                  25                  30

Ala Met His Trp Ile Arg Gln Pro Pro Gly Lys Gly Leu Asp Trp Val
        35                  40                  45

Ala Phe Ile Ser Ser Gly Gly Asp Thr Ala Tyr Ala Asp Ala Val Lys
    50                  55                  60

Gly Arg Phe Ile Val Ser Arg Asp Asn Ala Glu Asn Thr Leu Phe Leu
65                  70                  75                  80

Gln Leu Asn Ser Leu Lys Ser Glu Asp Thr Ala Ile Tyr Tyr Cys Val
                85                  90                  95

Arg Met Glu Arg Ile Pro Thr Trp Gly Gln Gly Val Met Val Thr Val
            100                 105                 110

Ser Ser

<210> SEQ ID NO 2
<211> LENGTH: 115
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Arg
1               5                   10                  15

Ser Leu Lys Leu Ser Cys Ala Ala Ser Asp Leu Thr Phe Ser Asn Tyr
            20                  25                  30

Asp Met Ala Trp Val Arg Gln Thr Pro Thr Lys Gly Leu Glu Trp Val
        35                  40                  45

Ala Ser Ile Ser Pro Asn Gly Gly Asn Thr Tyr Tyr Arg Asp Ser Val
    50                  55                  60

Lys Gly Arg Phe Thr Val Ser Arg Asp Asn Ala Lys Asn Ser Leu Tyr
65                  70                  75                  80

Leu Gln Met Asp Ser Leu Arg Ser Glu Asp Thr Ala Thr Tyr Tyr Cys
                85                  90                  95

Ala Arg His Leu Trp Phe Ala Tyr Trp Gly Gln Gly Thr Leu Val Thr
            100                 105                 110

Val Ser Ser
        115

<210> SEQ ID NO 3
<211> LENGTH: 120
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Gln Glu Ser Gly Pro Gly Leu Val Lys Pro Ser Gln
1               5                   10                  15

Ser Leu Ser Leu Thr Cys Ser Val Thr Tyr His Thr Ile Thr Ser Gly
            20                  25                  30
```

Tyr Asp Trp Thr Trp Ile Arg Lys Phe Pro Gly Asn Gln Met Glu Trp
            35                  40                  45

Met Gly Tyr Ile Ser Tyr Ser Gly Asn Thr Asn Tyr Asn Pro Ser Leu
 50                  55                  60

Lys Ser Arg Ile Ser Ile Thr Arg Asp Thr Ser Lys Asn Gln Phe Phe
65                  70                  75                  80

Leu His Leu Asn Ser Val Thr Ser Glu Asp Thr Ala Thr Tyr Tyr Cys
                85                  90                  95

Ala Ser Met Met Val Pro His Tyr Tyr Val Met Asp Ala Trp Gly Gln
            100                 105                 110

Gly Ala Ser Val Thr Val Ser Ser
            115                 120

<210> SEQ ID NO 4
<211> LENGTH: 119
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Gln Gln Ser Gly Pro Glu Ala Gly Arg Pro Gly Ser
1               5                   10                  15

Ser Val Lys Ile Ser Cys Lys Ala Ser Gly Tyr Thr Phe Thr Asn Tyr
            20                  25                  30

Phe Met Asn Trp Val Lys Gln Ser Pro Gly Gln Gly Leu Glu Trp Ile
            35                  40                  45

Gly Arg Val Asp Pro Glu Asn Gly Arg Ala Asp Tyr Ala Glu Lys Phe
 50                  55                  60

Lys Lys Lys Ala Thr Leu Thr Ala Asp Thr Thr Ser Asn Thr Ala Tyr
65                  70                  75                  80

Ile His Leu Ser Ser Leu Thr Ser Glu Asp Thr Ala Thr Tyr Phe Cys
                85                  90                  95

Ala Arg Arg Ala Met Asp Asn Tyr Gly Phe Ala Tyr Trp Gly Gln Gly
            100                 105                 110

Thr Leu Val Thr Val Ser Ser
            115

<210> SEQ ID NO 5
<211> LENGTH: 115
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Asp Leu Thr Phe Ser Asn Tyr
            20                  25                  30

Asp Met Ala Trp Val Arg Gln Ala Pro Gly Lys Gly Leu Glu Trp Val
            35                  40                  45

Ala Ser Ile Ser Pro Ser Gly Gly Asn Thr Tyr Tyr Arg Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

```
                    85                  90                  95

Ala Arg His Leu Trp Phe Ala Tyr Trp Gly Gln Gly Thr Leu Val Thr
                100                 105                 110

Val Ser Ser
        115

<210> SEQ ID NO 6
<211> LENGTH: 120
<212> TYPE: PRT
<213> ORGANISM: Artificial Sequence
<220> FEATURE:
<223> OTHER INFORMATION: Synthetic Construct

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Ser Val Thr Tyr His Thr Ile Thr Ser Gly
            20                  25                  30

Tyr Asp Trp Thr Trp Ile Arg Lys Pro Pro Gly Lys Gly Met Glu Trp
        35                  40                  45

Ile Gly Tyr Ile Ser Tyr Ser Gly Asn Thr Asn Tyr Asn Pro Ser Leu
    50                  55                  60

Lys Ser Arg Val Thr Ile Ser Arg Asp Thr Ser Lys Asn Gln Phe Phe
65                  70                  75                  80

Leu Lys Leu Ser Ser Val Thr Ala Ala Asp Thr Ala Val Tyr Tyr Cys
                85                  90                  95

Ala Ser Met Met Val Pro His Tyr Tyr Val Met Asp Ala Trp Gly Gln
                100                 105                 110

Gly Thr Leu Val Thr Val Ser Ser
        115                 120

<210> SEQ ID NO 7
<211> LENGTH: 119
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Phe Met Asn Trp Val Arg Gln Ala Pro Gly Gln Gly Leu Glu Trp Met
        35                  40                  45

Gly Arg Val Asp Pro Glu Gln Gly Arg Ala Asp Tyr Ala Glu Lys Phe
    50                  55                  60

Lys Lys Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ala Met Asp Asn Tyr Gly Phe Ala Tyr Trp Gly Gln Gly
                100                 105                 110

Thr Leu Val Thr Val Ser Ser
        115

<210> SEQ ID NO 8
<211> LENGTH: 110
```

```
<212> TYPE: PRT
<213> ORGANISM: Artificial Sequence
<220> FEATURE:
<223> OTHER INFORMATION: Synthetic Construct

<400> SEQUENCE: 8

Asp Ile Val Leu Thr Gln Ser Pro Val Leu Ala Val Ser Leu Gly Gln
1               5                   10                  15

Arg Ala Thr Ile Ser Cys Arg Ala Ser Gln Ser Val Ser Ile Ser Ser
            20                  25                  30

Ile Asn Leu Ile His Trp Tyr Gln Gln Arg Pro Gly Gln Gln Pro Lys
        35                  40                  45

Leu Leu Ile Tyr Arg Thr Ser Asn Leu Ala Ser Gly Ile Pro Ala Arg
    50                  55                  60

Phe Ser Gly Ser Gly Ser Gly Thr Asp Phe Thr Leu Ser Ile Asp Pro
65                  70                  75                  80

Val Gln Ala Asp Asp Val Ala Asp Tyr Tyr Cys Gln Gln Ser Arg Glu
                85                  90                  95

Ser Pro Leu Thr Phe Gly Ser Gly Thr Lys Leu Glu Ile Lys
            100                 105                 110

<210> SEQ ID NO 9
<211> LENGTH: 107
<212> TYPE: PRT
<213> ORGANISM: Artificial Sequence
<220> FEATURE:
<223> OTHER INFORMATION: Synthetic Construct

<400> SEQUENCE: 9

Asp Ile Gln Met Thr Gln Ser Pro Ser Ser Met Ser Ala Ser Leu Gly
1               5                   10                  15

Asp Arg Val Thr Ile Ser Cys Gln Ala Ser Gln Asp Ile Gly Ser Asn
            20                  25                  30

Leu Ile Trp Phe Gln Gln Lys Pro Gly Lys Ser Pro Arg Pro Met Ile
        35                  40                  45

Tyr Tyr Ala Thr His Leu Ala Asp Gly Val Pro Ser Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Val Ala Asp Tyr His Cys Leu Gln Tyr Lys Gln Tyr Pro Arg
                85                  90                  95

Thr Phe Gly Gly Gly Thr Lys Leu Glu Leu Lys
            100                 105

<210> SEQ ID NO 10
<211> LENGTH: 112
<212> TYPE: PRT
<213> ORGANISM: Artificial Sequence
<220> FEATURE:
<223> OTHER INFORMATION: Synthetic Construct

<400> SEQUENCE: 10

Asp Val Val Leu Thr Gln Thr Pro Pro Thr Ser Ser Ala Thr Ile Gly
1               5                   10                  15

Gln Ser Val Ser Ile Ser Cys Arg Ser Ser Gln Ser Leu Leu Asn Ser
            20                  25                  30

Asp Gly Asn Thr Tyr Leu Tyr Trp Tyr Leu Gln Arg Pro Ser Gln Ser
        35                  40                  45

Pro Gln Leu Leu Ile Tyr Leu Val Ser Lys Leu Gly Ser Gly Val Pro
```

```
                    50                  55                  60
Asn Arg Phe Ser Gly Ser Gly Ser Gly Thr Asp Phe Thr Leu Lys Ile
 65                  70                  75                  80

Ser Gly Val Glu Ala Glu Asp Leu Gly Leu Tyr Tyr Cys Val Gln Gly
                     85                  90                  95

Thr His Asp Pro Trp Thr Phe Gly Gly Gly Thr Lys Leu Glu Leu Lys
                100                 105                 110
```

<210> SEQ ID NO 11
<211> LENGTH: 106
<212> TYPE: PRT
<213> ORGANISM: Artificial Sequence
<220> FEATURE:
<223> OTHER INFORMATION: Synthetic Construct

<400> SEQUENCE: 11

```
Glu Ile Met Leu Thr Gln Ser Pro Thr Ile Met Ala Ala Ser Leu Gly
 1               5                  10                  15

Glu Lys Ile Thr Ile Thr Cys Ser Ala Asn Ser Ser Leu Ser Tyr Met
                 20                  25                  30

Tyr Trp Phe Gln Gln Lys Ser Gly Ala Ser Pro Lys Leu Trp Val His
             35                  40                  45

Gly Thr Ser Asn Leu Ala Ser Gly Val Pro Asp Arg Phe Ser Gly Ser
         50                  55                  60

Gly Ser Gly Thr Ser Tyr Tyr Leu Thr Ile Asn Thr Met Glu Ala Glu
 65                  70                  75                  80

Asp Ala Ala Thr Tyr Phe Cys His His Trp Ser Asn Thr Gln Trp Thr
                 85                  90                  95

Phe Gly Gly Gly Thr Lys Leu Glu Leu Lys
                100                 105
```

<210> SEQ ID NO 12
<211> LENGTH: 107
<212> TYPE: PRT
<213> ORGANISM: Artificial Sequence
<220> FEATURE:
<223> OTHER INFORMATION: Synthetic Construct

<400> SEQUENCE: 12

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Gly Ser Asn
                 20                  25                  30

Leu Ile Trp Phe Gln Gln Lys Pro Gly Lys Ala Pro Lys Pro Met Ile
             35                  40                  45

Tyr Tyr Ala Thr His Leu Ala Asp Gly Val Pro Ser Arg Phe Ser Gly
         50                  55                  60

Ser Arg Ser Gly Thr Asp Tyr Thr Leu Thr Ile Ser Ser Leu Gln Pro
 65                  70                  75                  80

Glu Asp Phe Ala Thr Tyr Tyr Cys Leu Gln Tyr Lys Gln Tyr Pro Arg
                 85                  90                  95

Thr Phe Gly Gly Gly Thr Lys Val Glu Ile Lys
                100                 105
```

<210> SEQ ID NO 13
<211> LENGTH: 112
<212> TYPE: PRT
<213> ORGANISM: Artificial Sequence
<220> FEATURE:

<223> OTHER INFORMATION: Synthetic Construct

<400> SEQUENCE: 13

Asp Ile Val Met Thr Gln Thr Pro Leu Ser Leu Ser Val Thr Pro Gly
1               5                   10                  15
Gln Pro Ala Ser Ile Ser Cys Arg Ser Ser Gln Ser Leu Leu Asn Ser
            20                  25                  30
Asp Gly Asn Thr Tyr Leu Tyr Trp Tyr Leu Gln Lys Pro Gly Gln Ser
        35                  40                  45
Pro Gln Leu Leu Ile Tyr Leu Val Ser Lys Leu Gly Ser Gly Val Pro
    50                  55                  60
Asn Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Val Gln Gly
                85                  90                  95
Thr His Asp Pro Trp Thr Phe Gly Gly Gly Thr Lys Val Glu Ile Lys
            100                 105                 110

<210> SEQ ID NO 14
<211> LENGTH: 106
<212> TYPE: PRT
<213> ORGANISM: Artificial Sequence
<220> FEATURE:
<223> OTHER INFORMATION: Synthetic Construct

<400> SEQUENCE: 14

Glu Ile Val Leu Thr Gln Ser Pro Asp Phe Gln Ser Val Thr Pro Lys
1               5                   10                  15
Glu Lys Val Thr Ile Thr Cys Ser Ala Asn Ser Ala Leu Ser Tyr Met
            20                  25                  30
Tyr Trp Tyr Gln Gln Lys Pro Asp Gln Ser Pro Lys Leu Trp Val His
        35                  40                  45
Gly Thr Ser Asn Leu Ala Ser Gly Val Pro Ser Arg Phe Ser Gly Ser
    50                  55                  60
Gly Ser Gly Thr Asp Phe Thr Leu Thr Ile Asn Ser Leu Glu Ala Glu
65                  70                  75                  80
Asp Ala Ala Thr Tyr Tyr Cys His His Trp Ser Asn Thr Gln Trp Thr
                85                  90                  95
Phe Gly Gly Gly Thr Lys Val Glu Ile Lys
            100                 105

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct

<400> SEQUENCE: 15

Met Glu Arg Ile Pro Thr
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct

<400> SEQUENCE: 16

```
His Leu Trp Phe Ala Tyr
1               5

<210> SEQ ID NO 17
<211> LENGTH: 11
<212> TYPE: PRT
<213> ORGANISM: Artificial Sequence
<220> FEATURE:
<223> OTHER INFORMATION: Synthetic Construct

<400> SEQUENCE: 17

Met Met Val Pro His Tyr Tyr Val Met Asp Ala
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic Construct

<400> SEQUENCE: 18

Arg Ala Met Asp Asn Tyr Gly Phe Ala Tyr
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Gln Gln Ser Arg Glu Ser Pro Leu Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Leu Gln Tyr Lys Gln Tyr Pro Arg Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Val Gln Gly Thr His Asp Pro Trp Thr
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

His His Trp Ser Asn Thr Gln Trp Thr
```

```
<210> SEQ ID NO 23
<211> LENGTH: 16
<212> TYPE: PRT
<213> ORGANISM: Artificial Sequence
<220> FEATURE:
<223> OTHER INFORMATION: Synthetic Construct

<400> SEQUENCE: 23

Phe Ile Ser Ser Gly Gly Asp Thr Ala Tyr Ala Asp Ala Val Lys Gly
1               5                   10                  15

<210> SEQ ID NO 24
<211> LENGTH: 17
<212> TYPE: PRT
<213> ORGANISM: Artificial Sequence
<220> FEATURE:
<223> OTHER INFORMATION: Synthetic Construct

<400> SEQUENCE: 24

Ser Ile Ser Pro Asn Gly Gly Asn Thr Tyr Tyr Arg Asp Ser Val Lys
1               5                   10                  15

Gly

<210> SEQ ID NO 25
<211> LENGTH: 16
<212> TYPE: PRT
<213> ORGANISM: Artificial Sequence
<220> FEATURE:
<223> OTHER INFORMATION: Synthetic Construct

<400> SEQUENCE: 25

Tyr Ile Ser Tyr Ser Gly Asn Thr Asn Tyr Asn Pro Ser Leu Lys Ser
1               5                   10                  15

<210> SEQ ID NO 26
<211> LENGTH: 17
<212> TYPE: PRT
<213> ORGANISM: Artificial Sequence
<220> FEATURE:
<223> OTHER INFORMATION: Synthetic Construct

<400> SEQUENCE: 26

Arg Val Asp Pro Glu Asn Gly Arg Ala Asp Tyr Ala Glu Lys Phe Lys
1               5                   10                  15

Lys

<210> SEQ ID NO 27
<211> LENGTH: 17
<212> TYPE: PRT
<213> ORGANISM: Artificial Sequence
<220> FEATURE:
<223> OTHER INFORMATION: Synthetic Construct

<400> SEQUENCE: 27

Ser Ile Ser Pro Ser Gly Gly Asn Thr Tyr Tyr Arg Asp Ser Val Lys
1               5                   10                  15

Gly

<210> SEQ ID NO 28
<211> LENGTH: 17
<212> TYPE: PRT
<213> ORGANISM: Artificial Sequence
<220> FEATURE:
```

-continued

<223> OTHER INFORMATION: Synthetic Construct

<400> SEQUENCE: 28

Arg Val Asp Pro Glu Gln Gly Arg Ala Asp Tyr Ala Glu Lys Phe Lys
1               5                   10                  15

Lys

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct

<400> SEQUENCE: 29

Arg Thr Ser Asn Leu Ala Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Tyr Ala Thr His Leu Ala Asp
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic Construct

<400> SEQUENCE: 31

Leu Val Ser Lys Leu Gly Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic Construct

<400> SEQUENCE: 32

Gly Thr Ser Asn Leu Ala Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct

<400> SEQUENCE: 33

Ser Ser Ala Met His
1               5

<210> SEQ ID NO 34
<211> LENGTH: 5
<212> TYPE: PRT
<213> ORGANISM: Artificial Sequence

```
<220> FEATURE:
<223> OTHER INFORMATION: Synthetic Construct

<400> SEQUENCE: 34

Asn Tyr Asp Met Ala
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic Construct

<400> SEQUENCE: 35

Ser Gly Tyr Asp Trp Thr
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Asn Tyr Phe Met Asn
1               5

<210> SEQ ID NO 37
<211> LENGTH: 15
<212> TYPE: PRT
<213> ORGANISM: Artificial Sequence
<220> FEATURE:
<223> OTHER INFORMATION: Synthetic Construct

<400> SEQUENCE: 37

Arg Ala Ser Gln Ser Val Ser Ile Ser Ser Ile Asn Leu Ile His
1               5                   10                  15

<210> SEQ ID NO 38
<211> LENGTH: 11
<212> TYPE: PRT
<213> ORGANISM: Artificial Sequence
<220> FEATURE:
<223> OTHER INFORMATION: Synthetic Construct

<400> SEQUENCE: 38

Gln Ala Ser Gln Asp Ile Gly Ser Asn Leu Ile
1               5                   10

<210> SEQ ID NO 39
<211> LENGTH: 16
<212> TYPE: PRT
<213> ORGANISM: Artificial Sequence
<220> FEATURE:
<223> OTHER INFORMATION: Synthetic Construct

<400> SEQUENCE: 39

Arg Ser Ser Gln Ser Leu Leu Asn Ser Asp Gly Asn Thr Tyr Leu Tyr
1               5                   10                  15

<210> SEQ ID NO 40
<211> LENGTH: 10
<212> TYPE: PRT
<213> ORGANISM: Artificial Sequence
<220> FEATURE:
```

<223> OTHER INFORMATION: Synthetic Construct

<400> SEQUENCE: 40

Ser Ala Asn Ser Ser Leu Ser Tyr Met Tyr
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Ser Ala Asn Ser Ala Leu Ser Tyr Met Tyr
1               5                   10

<210> SEQ ID NO 42
<211> LENGTH: 345
<212> TYPE: DNA
<213> ORGANISM: Artificial Sequence
<220> FEATURE:
<223> OTHER INFORMATION: Synthetic Construct

<400> SEQUENCE: 42

```
gaggtgcagc tggtggagag cggcggagga ctggtgcaac ctggcggaag cctgagactg      60
agctgcgccg ccagcgacct gaccttcagc aactacgaca tggcctgggt gagacaggcc    120
cctggcaagg gactggagtg ggtggccagc atcagcccca gcggcggcaa cacctactac    180
agggacagcg tgaagggcag gttcaccatc agcagggaca cgccaagaa cagcctgtac     240
ctgcagatga acagcctgag ggccgaggac accgccgtgt actactgcgc caggcacctg    300
tggttcgcct actggggcca gggcacactg gtgaccgtga gcagc                    345
```

<210> SEQ ID NO 43
<211> LENGTH: 360
<212> TYPE: DNA
<213> ORGANISM: Artificial Sequence
<220> FEATURE:
<223> OTHER INFORMATION: Synthetic Construct

<400> SEQUENCE: 43

```
caggtgcagc tgcaggagag cggacccgga ctggtgaagc cctccgagac cctgagcctg      60
acctgcagcg tgacctacca ccatcacc agcggctacg actggacctg gatcagaaag       120
ccccccggca aaggcatgga gtggatcggc tacatcagct acagcggcaa caccaactac    180
aaccccagcc tgaagagcag ggtgaccatc agcagggaca ccagcaagaa ccagttcttc    240
ctgaagctga gcagcgtgac agccgccgat accgccgtgt actactgcgc cagcatgatg    300
gtgccccact actacgtgat ggacgcctgg ggacagggca cctggtgac agtgagcagc     360
```

<210> SEQ ID NO 44
<211> LENGTH: 357
<212> TYPE: DNA
<213> ORGANISM: Artificial Sequence
<220> FEATURE:
<223> OTHER INFORMATION: Synthetic Construct

<400> SEQUENCE: 44

```
caggtgcagc tggtgcagag cggagccgag gtgaagaagc ccggcagcag cgtgaaggtg      60
agctgcaagg ccagcggcta caccttcacc aactacttca tgaactgggt gaggcaggcc    120
cctggacaag gcctggagtg gatgggcaga gtggatcccg agcagggcag ggccgactac    180
```

```
gccgagaagt tcaagaagag ggtgaccatc accgccgaca agagcaccag caccgcctac    240
atggagctga gcagcctgag gagcgaggac accgccgtgt actactgcgc caggagagcc    300
atggacaact acggcttcgc ctactggggc cagggaaccc tggtgaccgt gagcagc       357

<210> SEQ ID NO 45
<211> LENGTH: 321
<212> TYPE: DNA
<213> ORGANISM: Artificial Sequence
<220> FEATURE:
<223> OTHER INFORMATION: Synthetic Construct

<400> SEQUENCE: 45
gacatccaga tgacccagag ccctagcagc ctgagcgcca gcgtgggcga tagggtgacc     60
atcacctgcc aggccagcca ggacatcggc agcaacctga tctggttcca gcagaagccc    120
ggcaaggccc ccaagcctat gatctactac gccacccacc tggccgatgg cgtgcctagc    180
agattcagcg gcagcagaag cggcaccgac tacaccctga ccatcagcag cctgcagccc    240
gaggacttcg ccacctacta ctgcctgcag tacaagcagt accccagaac cttcggcggc    300
ggcaccaagg tggagatcaa g                                              321

<210> SEQ ID NO 46
<211> LENGTH: 336
<212> TYPE: DNA
<213> ORGANISM: Artificial Sequence
<220> FEATURE:
<223> OTHER INFORMATION: Synthetic Construct

<400> SEQUENCE: 46
gacatcgtga tgacccagac cccctgagc ctgagcgtga cacctggaca gcccgccagc      60
atcagctgca ggtccagcca gagcctgctg aacagcgacg gcaacaccta cctgtactgg    120
tacctgcaga agcctggcca gagccccag ctgctgatct acctggtgtc aagctgggc     180 agcggcgtgc ctaacaggtt tagcggcagc ggcagcggca ccgatttcac cctgaagatc    240
agcagggtgg aggccgagga tgtgggcgtg tactactgcg tgcagggcac ccacgatcct    300
tggaccttcg gcggcggaac caaggtggag atcaag                              336

<210> SEQ ID NO 47
<211> LENGTH: 318
<212> TYPE: DNA
<213> ORGANISM: Artificial Sequence
<220> FEATURE:
<223> OTHER INFORMATION: Synthetic Construct

<400> SEQUENCE: 47
gagatcgtgc tgacccagag ccccgacttc cagagcgtga cccccaagga aaggtgacc      60 atcacctgca gcgccaacag cgccctgagc tacatgtact ggtaccagca gaagcccgac    120
cagagcccca gctgtgggt gcacggcacc agcaatctgg ccagcggcgt gcctagcaga    180
tttagcggca gcggcagcgg caccgatttc accctgacca tcaacagcct ggaggccgag    240
gacgccgcta cctactactg ccaccactgg agcaacaccc agtggacctt cggcggcggc    300
accaaggtgg agatcaag                                                  318

<210> SEQ ID NO 48
<211> LENGTH: 6
<212> TYPE: PRT
<213> ORGANISM: Artificial Sequence
<220> FEATURE:
```

-continued

<223> OTHER INFORMATION: Synthetic Construct

<400> SEQUENCE: 48

Met Tyr Pro Pro Pro Tyr
1               5

MONOCLONAL ANTIBODIES TO CYTOTOXIC T-LYMPHOCYTE-ASSOCIATED PROTEIN 4 (CTLA-4)

CROSS REFERENCE TO RELATED APPLICATIONS

This application is a national stage application under 35 U.S.C. § 371 of International Application No. PCT/CN2017/085134, filed internationally on May 19, 2017.

TECHNICAL FIELD

The present invention relates generally to antibodies against CTLA-4 and compositions thereof, and immunotherapy in the treatment of cancer, infections or other human diseases using anti-CTLA-4 antibodies.

INCORPORATION-BY-REFERENCE OF SEQUENCE LISTING

This instant application contains a Sequence Listing which has been submitted electronically in ASCII format and is hereby incorporated by reference in its entirety. Said ASCII copy, created on Apr. 27, 2020, is named XTX101_SL.txt and is 85.7 KB in size.

BACKGROUND OF THE INVENTION

Cancer immunotherapy has become a hot research area of treating cancer. Cytotoxic T-lymphocyte-associated protein 4 (CTLA-4) is one of the validated targets of immune checkpoints. After T cell activation, CTLA-4 quickly expresses on those T cells, generally within one hour of antigen engagement with TCR. CTLA-4 can inhibit T cell signaling through competition with CD28. CD28 mediates one of well characterized T cell co-stimulatory signal: CD28 binding to its ligands CD80 (B7-1) and CD86 (B7-2) on antigen presenting cells leads to T cell proliferation by inducing production of interleukin-2 and anti-apoptotic factors. Due to much higher affinity binding of CTLA-4 to CD80 and CD86 than that of CD28, CTLA-4 can outcompete with CD28 binding on CD80 and CD86, leading to suppression of T cell activation. In addition to induced expression on activated T cells, CTLA-4 is constitutively expressed on the surface of regulatory T cells (Treg), suggesting that CTLA-4 may be required for contact-mediated suppression and associated with Treg production of immunosuppressive cytokines such as transforming growth factor beta and iterleukin-10.

CTLA-4 blockade can induce tumor regression, demonstrating in a number of preclinical and clinical studies. Two antibodies against CTLA-4 are in clinical development. Ipilimumab (MDX-010, BMS-734016), a fully human anti-CTLA-4 monoclonal antibody of IgG1-kappa isotype, is an immunomodulatory agent that has been approved as monotherapy for treatment of advanced melanoma. The proposed mechanism of action for Ipilimumab is interference of the interaction of CTLA-4, expressed on a subset of activated T cells, with CD80/CD86 molecules on professional antigen presenting cells. This results in T-cell potentiation due to blockade of the inhibitory modulation of T-cell activation promoted by the CTLA-4 and CD80/CD86 interaction. The resulting T-cell activation, proliferation and lymphocyte infiltration into tumors, leads to tumor cell death. The commercial dosage form is a 5 mg/mL concentrate for solution for infusion. Ipilimumab is also under clinical investigation of other tumor types, including prostate and lung cancers. Another anti-CTLA-4 antibody Tremelimumab was evaluated as monotherapy in melanoma and malignant mesothelioma.

DISCLOSURE OF THE INVENTION

The present invention provides isolated antibodies, in particular monoclonal antibodies or humanized monoclonal antibodies.

In one aspect, the present invention provides an antibody or an antigen binding-fragment thereof, wherein the antibody or the antigen binding-fragment binds to human, monkey and mouse CTLA-4.

The aforesaid antibody or the antigen binding-fragment inhibits CTLA-4 binding to CD80 or CD86.

In the aforesaid antibody or the antigen binding-fragment, binding epitope of the antibody or antigen binding-fragment comprises N145 or polysaccharide on N145 of CTLA-4.

In one aspect, the present invention provides an antibody or an antigen binding fragment thereof, wherein the antibody or the antigen binding fragment binds to human, monkey CTLA-4, wherein binding epitope of the antibody or antigen binding-fragment comprises P138 of CTLA-4.

In one aspect, the present invention provides an antibody or an antigen binding fragment thereof, wherein the antibody or the antigen binding-fragment a) binds to human CTLA-4 with a $K_D$ of 4.77 E-10 M or less; and b) binds to mouse CTLA-4 with a $K_D$ of 1.39 E-09 M or less.

The aforesaid antibody, wherein the antibody or the antigen binding-fragment exhibits at least one of the following properties:

a) binds to human CTLA-4 with a $K_D$ of between 4.77 E-10 M and 2.08 E-10 M and to mouse CTLA-4 with a $K_D$ of between 1.39 E-09 M and 9.06 E-10 M;

b) enhances interleukin-2 release from stimulated PBMCs.

c) does not substantially bind to any protein selected from a group consisting of Factor VIII, FGFR, PD-1, CD22, VEGF, CD3, HER3, OX40, and 4-1BB.

The present invention provides an antibody or an antigen binding fragment thereof, comprising an amino acid sequence that is at least 70%, 80%, 90% or 95% homologous to a sequence selected from a group consisting of SEQ ID NOs: 1, 2, 3, 4, 5, 6, 7, 8, 9, 10, 11, 12, 13, and 14, wherein the antibody or the antigen binding-fragment specifically binds to CTLA-4.

The present invention provides an antibody or an antigen binding fragment thereof, comprising an amino acid sequence selected from a group consisting of SEQ ID NOs: 1, 2, 3, 4, 5, 6, 7, 8, 9, 10, 11, 12, 13, and 14, wherein the antibody or the antigen binding-fragment specifically binds to CTLA-4.

The present invention provides an antibody, or an antigen-binding fragment thereof, comprising:

a) a variable region of a heavy chain having an amino acid sequence that is at least 70%, 80%, 90% or 95% homologous to a sequence selected from a group consisting of SEQ ID NOs: 1, 2, 3, 4, 5, 6, and 7; and b) a variable region of a light chain having an amino acid sequence that is at least 70%, 80%, 90% or 95% homologous to a sequence selected from a group consisting of SEQ ID NOs: 8, 9, 10, 11, 12, 13, and 14, wherein the antibody or the antigen binding-fragment specifically binds to CTLA-4.

The present invention provides an antibody or an antigen binding fragment thereof, comprising:

a) a variable region of a heavy chain having an amino acid sequence selected from the group consisting of SEQ ID NOs: 1, 2, 3, 4, 5, 6, and 7; and b) a variable region of a light chain having an amino acid sequence selected from the group consisting of SEQ ID NOs: 8, 9, 10, 11, 12, 13, and 14, wherein the antibody or the antigen binding-fragment specifically binds to CTLA-4.

In various embodiments, the antibody or an antigen binding fragment thereof comprises:

a) a variable region of a heavy chain having an amino acid sequence selected from the group consisting of SEQ ID NO: 1; and b) a variable region of a light chain having an amino acid sequence selected from the group consisting of SEQ ID NO: 8, wherein the antibody or the antigen binding-fragment specifically binds to CTLA-4;

or the antibody or an antigen binding fragment thereof comprises:

a) a variable region of a heavy chain having an amino acid sequence selected from the group consisting of SEQ ID NO: 2; and b) a variable region of a light chain having an amino acid sequence selected from the group consisting of SEQ ID NO: 9, wherein the antibody or the antigen binding-fragment specifically binds to CTLA-4;

or the antibody or an antigen binding fragment thereof comprises:

a) a variable region of a heavy chain having an amino acid sequence selected from the group consisting of SEQ ID NO: 3; and b) a variable region of a light chain having an amino acid sequence selected from the group consisting of SEQ ID NO: 10, wherein the antibody or the antigen binding-fragment specifically binds to CTLA-4;

or the antibody or an antigen binding fragment thereof comprises:

a) a variable region of a heavy chain having an amino acid sequence selected from the group consisting of SEQ ID NO: 4; and b) a variable region of a light chain having an amino acid sequence selected from the group consisting of SEQ ID NO: 11, wherein the antibody or the antigen binding-fragment specifically binds to CTLA-4;

or the antibody or an antigen binding fragment thereof comprises:

a) a variable region of a heavy chain having an amino acid sequence selected from the group consisting of SEQ ID NO: 5; and b) a variable region of a light chain having an amino acid sequence selected from the group consisting of SEQ ID NO: 12, wherein the antibody or the antigen binding-fragment specifically binds to CTLA-4;

or the antibody or an antigen binding fragment thereof comprises:

a) a variable region of a heavy chain having an amino acid sequence selected from the group consisting of SEQ ID NO: 6; and b) a variable region of a light chain having an amino acid sequence selected from the group consisting of SEQ ID NO: 13, wherein the antibody or the antigen binding-fragment specifically binds to CTLA-4;

or the antibody or an antigen binding fragment thereof comprises:

a) a variable region of a heavy chain having an amino acid sequence selected from the group consisting of SEQ ID NO: 7; and b) a variable region of a light chain having an amino acid sequence selected from the group consisting of SEQ ID NO: 14, wherein the antibody or the antigen binding-fragment specifically binds to CTLA-4;

The sequence of said antibody is shown in Table 1 and Sequence Listing.

TABLE 1

Deduced amino acid sequences of the antibodies

| Clone ID | | SEQ ID NO | Amino acid sequence |
|---|---|---|---|
| W3162-1.1 01.2 | Heavy chain | 1 | EEQLVESGGGLVQPGKGLKLSCSASGFTFRSSAMHQIRQPPGKGLDWVAF ISSGGDTAYADAVKGRFIVSRDNAENTLFLQLNSLKSEDTAIYYCVRMER IPTWGQGVMVTVSS |
| | Light chain | 8 | DIVLTQSPVLAVSLGQRATISCRASQSVSISISSINLIHWYQQRPGQQPKL LIYRTSNLASGIPARFSGSGSGTDFTLSIDPVQADDVADYYCQQSRESPL TFGSGTKLEIK |
| W3162-1. 145.10 | Heavy chain | 2 | EVQLVESGGGLVQPGRSLKLSCAASDLTFSNYDMAWVRQTPTKGLEWVAS ISPNGGNTYYRDSVKGRFTVSRDNAKNSLYLQMDSLRSEDTATYYCARHL WFAYWGQGTLVTVSS |
| | Light chain | 9 | DIQMTQSPSSMSASLGDRVTISCQASQDIGSNLIWFQQKPGKSPRPMIYY ATHLADGVPSRFSGSRSGSDYSLTISSLESEDVADYHCLQYKQYPRTFGG FTKLELK |
| W3162-1.1 46.19 | Heavy chain | 3 | EVQLQESGPGLVKPSQSLSLTCVTYHTITSGYDWTWIRKFPGNQMEWMGY ISYSGNTNYNPSLKSRISITRDTSKNQFFLHLNSVTSEDTATYYCASMMV PHYYVMDAWGQGASVTVSS |
| | Light chain | 10 | DVVLTQTPPTSSATIGQSVSISCRSSQSLLNSDGNTYLYWYLRQRPSQSP QLLIYLVSKLGSGVPNRFSGSGSGTDFTLKISGVEAEDLGLYYCVQGTHD PWTFGGGTKLELK |
| W3162-1.1 54.8 | Heavy chain | 4 | EVQLQQSGPEAGRPGSSVKISCKASGYTFTNYFMNWVKQSPGQGLEWIGR VDPENGRADYAEKFKKKATLTADTTSNTAYIHLSSLTSEDTATYFCARRA MDNYGFAYWGQGTLVTVSS |

TABLE 1-continued

Deduced amino acid sequences of the antibodies

| Clone ID | | SEQ ID NO | Amino acid sequence |
|---|---|---|---|
| | Light chain | 11 | EIMLTQSPTIMAASLGEKITITCSANSSLSYMYWFQQKSGASPKLWVHGT SNLASGVPDRFSGSGSGTSYYLTINTMEAEDAATYFCHHWSNTQWTFGGG TKLELK |
| W3162-1.1 45.10-z7 | Heavy chain | 5 | EVQLVESGGGLVQPGGSLRLSCAASDLTFSNYDMAWVRQAPGKGLEWVAS ISPSGGNTYYRDSVKGRFTISRDNAKNSLYLQMNSLRAECTAVYYCARHL WFAYWGQGTLVTVSS |
| | Light chain | 12 | DIQMTQSPSSLSASVGDRVTITCQASQDIGSNLIWFQQKPGKAPKPMIYY ATHLADGVPSRFSGSRSGTDYTLTISSLQPEDFATYYCLQYKQYPRTFGG GTKVEIK |
| W3162.1.14 6.-z12 | Heavy chain | 6 | QVQLQESGPGLVKPSETLSLTCSVTYHTITSGYDWTWIRKPPGKGMEWIG YISYSGNTNYNPSLKSRVTISEDTSKNQFFLKLSSVTAADTAVYYCASMM VPHYYVMDAWGQGTLVTVSS |
| | Light chain | 13 | DIVMTQTPLSLSVTPGQPASISCRSSQSLLNSDGNTYLYWYLQKPGQSPQ LLIYLVSKLGSGVPNRFSGSGSGTDFTLKISRVEAEDVGVYYCVQGTHDP WTFGGGTKVEIK |
| W3162.1.15 4.8-z35 | Heavy chain | 7 | QVQLVQSGAEVKKPGSSVKVSCKASGYTFTNYFMNWVRQAPGQGLEWMGR VDPEQGRADYAEKFKKRVTITADKSTSTAYMELSSLRSEDTAVYYCARRA MDNYGFAYWGQGTLVTVSS |
| | Light chain | 14 | EIVLTQSPDFQSVTPKEKVTITCSANSALSYMYWYQQKPDQSPKLWVHGT SNLASGVPSRFSGSGSGTDFTLTINSLEAEDAATYYCHHWSNTQWTFGGG TKVEIK |

In another aspect, the invention provides an antibody or an antigen binding fragment thereof, comprising a complementarity-determining region (CDR) having an amino acid sequence selected from the group consisting of SEQ ID NOs: 15-41, wherein the antibody or the antigen binding-fragment specifically binds to CTLA-4.

In another aspect, the invention provides an antibody, or an antigen binding fragment thereof, comprising: a heavy chain variable region comprising CDR1, CDR2, and CDR3 sequences; and a light chain variable region comprising CDR1, CDR2, and CDR3 sequences, wherein the heavy chain variable region CDR3 sequence comprises an amino acid sequence selected from a group consisting of SEQ ID NOs: 15, 16, 17, and 18, and conservative modifications thereof, wherein the antibody or the antigen binding-fragment specifically binds to CTLA-4.

Preferably, wherein the light chain variable region CDR3 sequence of the aforesaid antibody or antigen binding fragment thereof comprises an amino acid sequence selected from a group consisting of SEQ ID NOs: 19, 20, 21, and 22, and conservative modifications thereof.

Preferably, wherein the heavy chain variable region CDR2 sequence of the aforesaid antibody or antigen binding fragment thereof comprises an amino acid sequence selected from a group consisting of amino acid sequences of SEQ ID NOs: 23, 24, 25, 26, 27, and 28, and conservative modifications thereof.

Preferably, wherein the light chain variable region CDR2 sequence of the aforesaid antibody or antigen binding fragment thereof comprises an amino acid sequence selected from a group consisting of amino acid sequences of SEQ ID NOs: 29, 30, 31, and 32, and conservative modifications thereof.

Preferably, wherein the heavy chain variable region CDR1 sequence of the aforesaid antibody or antigen binding fragment thereof comprises an amino acid sequence selected from a group consisting of amino acid sequences of SEQ ID NOs: 33, 34, 35, and 36, and conservative modifications thereof.

Preferably, the antibody of this invention, wherein the light chain variable region CDR1 sequence of the aforesaid antibody or antigen binding fragment thereof comprises an amino acid sequence selected from a group consisting of amino acid sequences of SEQ ID NOs: 37, 38, 39, 40, and 41, and conservative modifications thereof.

In more preferred embodiment, the invention provides an antibody, or an antigen binding fragment thereof, wherein the antibody or antigen binding fragment specifically binds to CTLA-4 and comprises: a heavy chain variable region that comprises CDR1, CDR2, and CDR3 sequences; and a light chain variable region that comprises CDR1, CDR2, and CDR3 sequences, wherein:

a) the heavy chain variable region CDR1 sequence comprises an amino acid sequence selected from a group consisting of amino acid sequences of SEQ ID NOs: 33, 34, 35, and 36, and CDR2 sequence comprises an amino acid sequence selected from a group consisting of amino acid sequences of SEQ ID NOs: 23, 24, 25, 26, 27, and 28, CDR3 sequence comprises an amino acid sequence selected from a group consisting of amino acid sequences of SEQ ID NOs: 15, 16, 17, and 18;

b) and the light chain variable region CDR1 sequence comprises an amino acid sequence selected from a group consisting of amino acid sequences of SEQ ID NOs: 37, 38, 39, 40, and 41, and CDR2 sequence comprises an amino acid sequence selected from a group consisting of amino acid sequences of SEQ ID NOs: 29, 30, 31, and 32, CDR3 sequence comprises an amino acid sequence selected from a group consisting of amino acid sequences of SEQ ID NOs: 19, 20, 21, and 22, wherein the antibody or the antigen binding-fragment specifically binds to CTLA-4.

A preferred antibody or an antigen binding fragment thereof comprises:

a) a heavy chain variable region CDR1 comprising SEQ ID NO: 15;

b) a heavy chain variable region CDR2 comprising SEQ ID NO: 23;

c) a heavy chain variable region CDR3 comprising SEQ ID NO: 33;
d) a light chain variable region CDR1 comprising SEQ ID NOs: 19;
e) a light chain variable region CDR2 comprising SEQ ID NOs: 29;
f) a light chain variable region CDR3 comprising SEQ ID NOs: 37;
wherein the antibody or the antigen binding-fragment specifically binds to CTLA-4.

Another preferred antibody or an antigen binding fragment thereof comprises:
a) a heavy chain variable region CDR1 comprising SEQ ID NO: 16;
b) a heavy chain variable region CDR2 comprising SEQ ID NOs: 24;
c) a heavy chain variable region CDR3 comprising SEQ ID NOs: 34;
d) a light chain variable region CDR1 comprising SEQ ID NOs: 20;
e) a light chain variable region CDR2 comprising SEQ ID NO: 30;
f) a light chain variable region CDR3 comprising SEQ ID NO: 38;
wherein the antibody or the antigen binding-fragment specifically binds to CTLA-4.

Another preferred antibody or an antigen binding fragment thereof comprises:
a) a heavy chain variable region CDR1 comprising SEQ ID NO: 17;
b) a heavy chain variable region CDR2 comprising SEQ ID NO: 25;
c) a heavy chain variable region CDR3 comprising SEQ ID NO: 35;
d) a light chain variable region CDR1 comprising SEQ ID NO: 19;
e) a light chain variable region CDR2 comprising SEQ ID NO: 31;
f) a light chain variable region CDR3 comprising SEQ ID NO: 39;
wherein the antibody or the antigen binding-fragment specifically binds to CTLA-4.

Another preferred antibody or an antigen binding fragment thereof comprises:
a) a heavy chain variable region CDR1 comprising SEQ ID NO: 18;
b) a heavy chain variable region CDR2 comprising SEQ ID NO: 26;
c) a heavy chain variable region CDR3 comprising SEQ ID NO: 36;
d) a light chain variable region CDR1 comprising SEQ ID NO: 22;
e) a light chain variable region CDR2 comprising SEQ ID NO: 32;
f) a light chain variable region CDR3 comprising SEQ ID NO: 40;
wherein the antibody specifically binds to CTLA-4.

Another preferred antibody or an antigen binding fragment thereof comprises:
a) a heavy chain variable region CDR1 comprising SEQ ID NO: 16;
b) a heavy chain variable region CDR2 comprising SEQ ID NO: 27;
c) a heavy chain variable region CDR3 comprising SEQ ID NO: 34;
d) a light chain variable region CDR1 comprising SEQ ID NO: 20;
e) a light chain variable region CDR2 comprising SEQ ID NO: 30;
f) a light chain variable region CDR3 comprising SEQ ID NO: 38;
wherein the antibody or the antigen binding-fragment specifically binds to CTLA-4.

Another preferred antibody or an antigen binding fragment thereof comprises:
a) a heavy chain variable region CDR1 comprising SEQ ID NO: 17;
b) a heavy chain variable region CDR2 comprising SEQ ID NO: 25;
c) a heavy chain variable region CDR3 comprising SEQ ID NO: 35;
d) a light chain variable region CDR1 comprising SEQ ID NO: 21;
e) a light chain variable region CDR2 comprising SEQ ID NO: 31;
f) a light chain variable region CDR3 comprising SEQ ID NO: 39;
wherein the antibody or the antigen binding-fragment specifically binds to CTLA-4.

Another preferred antibody or an antigen binding fragment thereof comprises:
a) a heavy chain variable region CDR1 comprising SEQ ID NO: 18;
b) a heavy chain variable region CDR2 comprising SEQ ID NO: 28;
c) a heavy chain variable region CDR3 comprising SEQ ID NO: 36;
d) a light chain variable region CDR1 comprising SEQ ID NO: 22;
e) a light chain variable region CDR2 comprising SEQ ID NO: 32;
f) a light chain variable region CDR3 comprising SEQ ID NO: 41;
wherein the antibody or the antigen binding-fragment specifically binds to CTLA-4.

The CDR sequences of said antibodies are shown in Table 2 and Sequence Listing.

TABLE 2

The CDR sequences of the antibodies

| | | SEQ ID NO | CDR1 | SEQ ID NO | CDR2 | SEQ ID NO | CDR3 |
|---|---|---|---|---|---|---|---|
| W3162-1.1 | Heavy chain | 33 | SSAMH | 23 | FISSGGDTAYADAVKG | 15 | MERIPT |
| | Light chain | 37 | RASQSVSISSINLIH | 29 | RTSNLAS | 19 | QQSRESPLT |
| W3162-1.1 45.10 | Heavy chain | 34 | NYDMA | 24 | SISPNGGNTYYRDSVKG | 16 | HLWFAY |
| | Light chain | 38 | QASQDIGSNLI | 30 | YATHLAD | 20 | LQYKQYPRT |
| W3162-1.1 46.19 | Heavy chain | 35 | SGYDWT | 25 | YISYSGNTNYNPSLKS | 17 | MMVPHYYVMDA |
| | Light chain | 39 | RSSQSLLNSDGNTYLY | 31 | LVSKLGS | 21 | VQGTHDPWT |

TABLE 2-continued

The CDR sequences of the antibodies

| | | SEQ ID NO | CDR1 | SEQ ID NO | CDR2 | SEQ ID NO | CDR3 |
|---|---|---|---|---|---|---|---|
| W3162-1.1 54.8 | Heavy chain | 36 | NYFMN | 26 | RVDPENGRADYAEKFKK | 18 | RAMDNYGFAY |
| | Light chain | 40 | SANSSLSYMY | 32 | GTSNLAS | 22 | HHWSNTQWT |
| W3162-1.1 45.10-z7 | Heavy chain | 34 | NYDMA | 27 | SISPSGGNTYYRDSVKG | 16 | HLWFAY |
| | Light chain | 38 | QASQDIGSNLI | 30 | YATHLAD | 20 | LQYKQYPRT |
| W3162.1.14 6.-z12 | Heavy chain | 35 | SGYDWT | 25 | YISYSGNTNYNPSLKS | 17 | MMVPHYYVMDA |
| | Light chain | 39 | RSSQSLLNSDGNTYLY | 31 | LVSKLGS | 21 | VQGTHDPWT |
| W3162.1.15 4.8-z35 | Heavy chain | 36 | NYFMN | 28 | RVDPEQGRADYAEKFKK | 18 | RAMDNYGFAY |
| | Light chain | 41 | SANSALSYMY | 32 | GTSNLAS | 22 | HHWSNTQWT |

The antibodies of the invention can be chimeric antibody.

The antibodies of the invention can be humanized antibody.

The antibodies of the invention can be fully human antibody.

The antibodies of the invention can be rat antibody.

The antibodies or the antigen binding fragment thereof of the invention can exhibit at least one of the following properties:

a) binds to human CTLA-4 with a $K_D$ of 2.08 E-09 M or less and/or to mouse CTLA-4 with a $K_D$ of 1.39 E-09 M or less;

b) enhances interleukin-2 release from the stimulated PBMCs;

In a further aspect, the invention provides a nucleic acid molecule encoding the antibody, or antigen binding fragment thereof.

The invention provides a cloning or expression vector comprising the nucleic acid molecule encoding the antibody, or antigen binding fragment thereof.

The invention also provides a host cell comprising one or more cloning or expression vectors.

In yet another aspect, the invention provides a process, comprising culturing the host cell of the invention and isolating the antibody, wherein the antibody is prepared through immunization in a SD rat with human CTLA-4 extracellular domain and mouse CTLA-4 extracellular domain.

The invention provides a transgenic animal such as rat comprising human immunoglobulin heavy and light chain transgenes, wherein the rat expresses the antibody of this invention.

The invention provides hybridoma prepared from the rat of this invention, wherein the hybridoma produces said antibody.

In a further aspect, the invention provides pharmaceutical composition comprising the antibody, or the antigen binding fragment of said antibody in the invention, and one or more of a pharmaceutically acceptable excipient, a diluent or a carrier.

The invention provides an immunoconjugate comprising said antibody, or antigen-binding fragment thereof in this invention, linked to a therapeutic agent.

Wherein, the invention provides a pharmaceutical composition comprising said immunoconjugate and one or more of a pharmaceutically acceptable excipient, a diluent or a carrier.

The invention also provides a method for preparing an anti-CTLA-4 antibody or an antigen-binding fragment thereof comprising:

(a) providing:

(i) a heavy chain variable region antibody sequence comprising a CDR1 sequence that is selected from a group consisting of SEQ ID NOs: 33-36, a CDR2 sequence that is selected from a group consisting of SEQ ID NOs: 23-28; and a CDR3 sequence that is selected from the group consisting of SEQ ID NOs: 15-18; and/or (ii) a light chain variable region antibody sequence comprising a CDR1 sequence that is selected from the group consisting of SEQ ID NOs: 37-41, a CDR2 sequence that is selected from the group consisting of SEQ ID NOs: 29-32, and a CDR3 sequence that is selected from the group consisting of SEQ ID NOs: 19-22; and (b) expressing the altered antibody sequence as a protein.

The invention also provides a method of modulating an immune response in a subject comprising administering to the subject the antibody, or antigen binding fragment of any one of said antibodies in this invention.

The invention also provides the use of said antibody or the antigen binding fragment thereof in the manufacture of a medicament for the treatment or prophylaxis of an immune disorder or cancer.

The invention also provides a method of inhibiting growth of tumor cells in a subject, comprising administering to the subject a therapeutically effective amount of said antibody, or said antigen-binding fragment to inhibit growth of the tumor cells.

Wherein, the invention provides the method, wherein the tumor cells are of a cancer selected from a group consisting of melanoma, renal cancer, prostate cancer, breast cancer, colon cancer, lung cancer, bone cancer, pancreatic cancer, skin cancer, cancer of the head or neck, cutaneous or intraocular malignant melanoma, uterine cancer, ovarian cancer, and rectal cancer.

Wherein, the invention provides the method, wherein the antibody is a chimeric antibody, humanized antibody, human antibody or rat antibody.

The Features and Advantages of this Invention

The inventors have generated humanized antibodies against CTLA-4 utilizing the proprietary hybridoma technology, wherein the antibodies inhibited CTLA-4 binding to its ligands CD80 and CD86. The antibodies reported in this invention have high binding affinity, specifically binding to both human and monkey CTLA-4 protein; and potent modulating immune responses and increasing interleukin-2 production.

One of the antibodies not only bound to human and monkey CTLA-4, but also bound to murine CTLA-4, which could greatly facilitate preclinical validation of its efficacy in mouse tumor models.

DETAILED DESCRIPTION

Figure 1:
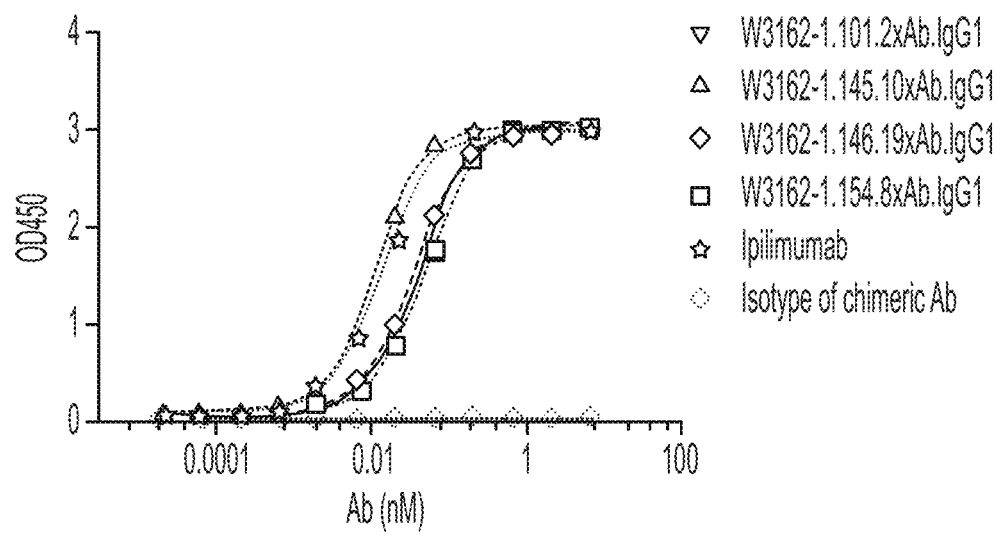
FIG. 1 shows graphs of chimeric antibodies binding to human CTLA-4 in ELISA.

In order that the present invention may be more readily understood, certain terms are first defined. Additional definitions are set forth throughout the detailed description.

The terms "Cytotoxic T lymphocyte-associated antigen-4", "Protein CTLA-4", "CTLA-4", "CTLA4", "CD152" are used interchangeably, and include variants, isoforms, species homologs of human CTLA-4 or CTLA-4 of other species, and analogs having at least one common epitope with CTLA-4.

The term "antibody" as referred to herein includes whole antibodies and any antigen-binding fragment (i.e., "antigen-binding portion") or single chains thereof. An "antibody" refers to a protein comprising at least two heavy (H) chains and two light (L) chains inter-connected by disulfide bonds, or an antigen-binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

The term "antibody," as used in this disclosure, refers to an immunoglobulin or a fragment or a derivative thereof, and encompasses any polypeptide comprising an antigen-binding site, regardless whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. The term "antibody" also includes antibody fragments such as Fab, F(ab')2, Fv, scFv, Fd, dAb, and other antibody fragments that retain antigen-binding function, i.e., the ability to bind CTLA-4 specifically. Typically, such fragments would comprise an antigen-binding fragment.

The terms "antigen-binding fragment," "antigen-binding domain," and "binding fragment" refer to a part of an antibody molecule that comprises amino acids responsible for the specific binding between the antibody and the antigen. In instances, where an antigen is large, the antigen-binding fragment may only bind to a part of the antigen. A portion of the antigen molecule that is responsible for specific interactions with the antigen-binding fragment is referred to as "epitope" or "antigenic determinant."

An antigen-binding fragment typically comprises an antibody light chain variable region (VL) and an antibody heavy chain variable region (VH), however, it does not necessarily have to comprise both. For example, a so-called Fd antibody fragment consists only of a VH domain, but still retains some antigen-binding function of the intact antibody.

In line with the above the term "epitope" defines an antigenic determinant, which is specifically bound/identified by a binding fragment as defined above. The binding fragment may specifically bind to/interact with conformational or continuous epitopes, which are unique for the target structure, e.g. the human CTLA-4 and murine CTLA-4. A conformational or discontinuous epitope is characterized for polypeptide antigens by the presence of two or more discrete amino acid residues which are separated in the primary sequence, but come together on the surface of the molecule when the polypeptide folds into the native protein/antigen. The two or more discrete amino acid residues contributing to the epitope are present on separate sections of one or more polypeptide chain(s). These residues come together on the surface of the molecule when the polypeptide chain(s)

fold(s) into a three-dimensional structure to constitute the epitope. In contrast, a continuous or linear epitope consists of two or more discrete amino acid residues, which are present in a single linear segment of a polypeptide chain.

The term "binds to an epitope of CTLA-4" refers to the antibodies have specific binding for a particular epitope of CTLA-4, which may be defined by a linear amino acid sequence, or by a tertiary, i.e., three-dimensional, conformation on part of the CTLA-4 polypeptide. Binding means that the antibodies affinity for the portion of CTLA-4 is substantially greater than their affinity for other related polypeptides. The term "substantially greater affinity" means that there is a measurable increase in the affinity for the portion of CTLA-4 as compared with the affinity for other related polypeptides. Preferably, the affinity is at least 1.5-fold, 2-fold, 5-fold 10-fold, 100-fold, $10^3$-fold, $10^4$-fold, $10^5$-fold, $10^6$-fold or greater for the particular portion of CTLA-4 than for other proteins. Preferably, the binding affinity is determined by enzyme-linked immunoabsorbent assay (ELISA), or by fluorescence-activated cell sorting (FACS) analysis or surface Plasmon resonance (SPR). More preferably, the binding specificity is obtained by fluorescence-activated cell sorting (FACS) analysis.

The term "cross-reactivity" refers to binding of an antigen fragment described herein to the same target molecule in human, monkey, and/or murine (mouse or rat). Thus, "cross-reactivity" is to be understood as an interspecies reactivity to the same molecule X expressed in different species, but not to a molecule other than X. Cross-species specificity of a monoclonal antibody recognizing e.g. human CTLA-4, to monkey, and/or to a murine (mouse or rat) CTLA-4, can be determined, for instance, by FACS analysis.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc. Except when noted, the terms "patient" or "subject" are used interchangeably.

The terms "treatment" and "therapeutic method" refer to both therapeutic treatment and prophylactic/preventative measures. Those in need of treatment may include individuals already having a particular medical disorder as well as those who may ultimately acquire the disorder.

The terms "conservative modifications" i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into the sequence by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The experimental methods in the following examples are conventional methods, unless otherwise specified.

EXAMPLES

Example 1: Research Materials Preparation

1. Expression and Purification of Soluble CTLA-4

Human and mouse CTLA-4 extracellular domain (ECD) genes with hexahistidine (6×His)- or Fc-tag were cloned into expression vector, and then used for transfection of Expi293 cells using Expi293 Expression System Kit. The cells were cultured in Expi293 Expression Medium, on an orbital shaker platform rotating at 135 rpm, in a 37° C. incubator containing a humidified atmosphere with 8% $CO_2$. The harvested supernatant was used for protein purification. Hexahistidine-tagged proteins were purified using Ni-NTA column and Fc-tagged proteins were purified using Protein A column.

2. Cell Lines Development

The gene of full length Human CTLA-4 was cloned into an expression vector for development of stable cell line. Briefly, a volume of 30 mL 293F cells at a density of $1 \times 10^6$/mL was transfected with 30 μg DNA using Plasfect Reagent. The transfected cells were put into in an incubator setting at 37° C., 8% $CO_2$ and 100 rpm shaking speed. 24-48 hours after transfection, blasticidin at a final concentration of 4-6 μg/mL was used to select the stable clones. The selected clones were tested by FACS using an anti-CTLA-4 antibody.

In order to obtain cells expressing cynomolgus monkey CTLA-4, the gene of full length cynomolgus monkey CTLA-4 was cloned into an expression vector for development of cell pool. Briefly, a volume of 30 mL 293F cells at a density of $1 \times 10^6$/mL was transfected with 30 μg DNA using Plasfect Reagent (Life Technology). The transfected cells were put into in an incubator setting at 37° C., 8% $CO_2$ and 100 rpm shaking speed. 24 hours after transfection, blasticidin at a final concentration of 4 μg/mL was used to select the cell pool. The selected cell pools were tested by FACS using an anti-CTLA-4 antibody

Example 2: Antibody Hybridoma Generation

1. Immunization

Human CTLA-4 and murine CTLA-4 were used for immunization of SD rats. Specifically, three SD rats were immunized with 30 μg/animal of human and mouse CTLA-4 ECD protein in adjuvant. The adjuvant included Titer-Max, Adju-Phos and CpG-ODN. The rats were injected once a week both from footpad and subcutaneously. The antibody titer in serum was measured by ELISA every one month. When the antibody titer was sufficiently high, the rat with the highest titer was given a final boost with human and mouse CTLA-4 ECD protein in Dulbecco's Phosphate Buffered Saline (DPBS) without adjuvant. After several days, the spleen and lymph nodes were taken from the rat, and lymphocytes were separated for fusion.

2. Cell Fusion

The cell fusion was performed as following: myeloma cells SP2/0 cells were thawed the week before the fusion, and were split at 1:2 every day until the day before the fusion to keep them in logarithmic growth. B lymphocytes isolated from lymph node of immunized rat and myeloma cells were respectively treated with trypsin and the reaction was stopped by adding FBS. B lymphocytes were combined with myeloma cells at 1:1 ratio. The cell mixture was then washed and re-suspended at $2 \times 10^6$ cells/ml in electric fusion solution containing 0.3 M sucrose, 0.1 mM magnesium acetate and 0.1 mM calcium acetate. The electric cell fusion was conducted using Btx Electro Cell Manipulator (Ecm 2001)

following the manufacturer's standard protocol. Then the cell suspension from the fusion chamber was immediately transferred into a sterile flask containing fresh medium, and incubated for 2 hours in 37° C. incubator. The cell suspension was then mixed and transferred into 60 of 96-well plates ($1\times10^4$ cells/well). The 96-well plates were cultured at 37° C. and 5% $CO_2$ with periodically monitoring. When the clones were big enough (after 7-10 days), 180 μL/well of supernatant were removed and then 200 μL fresh medium per well was add. After 72 hours, 100 μL of supernatant were transferred from the tissue culture plates to 96-well assay plates for screening.

3. Hybridoma Screening

A large number of hybridoma clones were screened on binding to human, murine and monkey CTLA-4 proteins as well as engineered human CTLA-4 expressing cells. Once specific CTLA-4 binding and blocking activity were verified through first and second screening, the positive hybridoma lines were subcloned into 96-well plates using limited dilution. The plates were cultured at 37° C., 5% $CO_2$ until the positive clones were further screened for competition with ligands CD80 and CD86 binding to CTLA-4. The cultural supernatants of selected positive clones were collected for antibodies purification and further characterization. The lead candidates were selected for VH and VL sequencing.

4. Determination of VH and VL Sequences from Hybridoma

The VH and VL genes of the antibodies of selected hybridoma clones were isolated by RT-PCR or 5' RACE. Specifically, total RNA was isolated from hybridoma cells by using RNeasy Plus Mini Kit (Qiagen). The first strand cDNA was reverse transcribed using oligo dT. VH and VL genes of the antibodies were amplified from cDNA using 3'-constant region degenerated primer and 5'-degenerated primer sets. The 5' degenerated primers were designed based on the upstream signal sequence-coding region of Ig variable sequences. The PCR product was then ligated into pMD18-T vector and 10 μL of the ligation product was transformed into Top10 competent cells. Transformed cells were plated on 2×YT plates with carbenicillin and incubated overnight at 37° C. 15 positive colonies were randomly picked for DNA sequencing by Biosune. Alternatively, 5' RACE was used to identify the VH and VL sequences of selected hybridoma clones. First, RNA was first reverse transcribed into cDNA using 5'-RACE kit (Takara-28001488), followed by PCR using 3'-degenerated primers and 3'-adaptor primers (ExTaq: Takara-RR001B). PCR fragments was inserted into pMD18-T vector (Takara-D101C) and sent for sequencing (Biosune, Shanghai).

Example 3: Chimeric Antibodies Production and Characterization

1. Chimeric Antibody Production

The deduced amino acid sequences of VH and VL are listed in the Table 3. Underlined sequences are CDRs defined by Kabat delineation system. The variable regions of these rat antibodies were fused with constant region of human antibody, and the chimeric antibodies were expressed from Expi293 cells and purified using Protein A chromatography.

TABLE 3

The variable region sequence of rat anti-CTLA-4 antibodies

| Clone ID | | SEQ ID NO | Amino acid sequence |
|---|---|---|---|
| W3162-1.101.2 | VH | 1 | EEQLVESGGGLVQPGKGLKLSCSASGFTFRSSAMHWIRQPPGKGL DWVAFISSGGDTAYADAVKGRFIVSRDNAENTLFLQLNSLKSEDT AIYYCVRMERIPTWGQGVMVTVSS |
| | VL | 8 | DIVLTQSPVLAVSLGQRATISCRASQSVSISSINLIHWYQQRPGQ QPKLLIYRTSNLASGIPARFSGSGSGTDFTLSIDPVQADDVADYY CQQSRESPLTFGSGTKLEIK |
| W3162-1.145.10 | VH | 2 | EVQLVESGGGLVQPGRSLKLSCAASDLTFSNYDMAWVRQTPTKGL EWVASISPNGGNTYYRDSVKGRFTVSRDNAKNSLYLQMDSLRSED TATYYCARHLWFAYWGQGTLVTVSS |
| | VL | 9 | DIQMTQSPSSMSASLGDRVTISCQASQDIGSNLIWFQQKPGKSPR PMIYYATHLADGVPSRFSGSRSGSDYSLTISSLESEDVADYHCLQ YKQYPRTFGGGTKLELK |
| W3162-1.146.19 | VH | 3 | EVQLQESGPGLVKPSQSLSLTCSVTHYTITSGYDWTWIRKFPGNQ MEWMGYISYSGNTNYNPSLKSRISITRDTSKNQFFLHLNSVTSED TATYYCASMMVPHYYVMDAWGQGASVTVSS |
| | VL | 10 | DVVLTQTPPTSSATIGQSVSISVRSSQSLLNSDGNTYLYWYLQRP SQSPQLLIYLVSKLGSGVPNRFSGSGSGTDFTLKISGVEAEDLGL YYCVQGTHDPWTFGGGTKLELK |
| W3162-1.154.8 | VH | 4 | EVQLQQSGPEAGRPGSSVKISCKASGYTFTNYFMNWVKQSPGQGL EWIGRVDPENGRADYAEKFKKKATLTADTTSNTAYIHLSSLTSED TATYFCARRAMDNYGFAYWGQGLTVTVSS |
| | VL | 11 | EIMLTQSPTIMAASLGEKITITCSANSSLSYMYWFQQKSGASPKL WVHGTSNLASGVPDRFSGSGSGTSYYLTINTMEAEDAATYFCHHW SNTQWTFGGGTKLELK |

2. Characterization of Chimeric Antibodies 2.1 Antibodies Bound to Human, Monkey and Murine CTLA-4 (ELISA, FACS and SPR)

Chimeric antibodies with rat variable region and human constant region were expressed from mammalian cells and purified using Protein A affinity chromatography.

Figure 2:
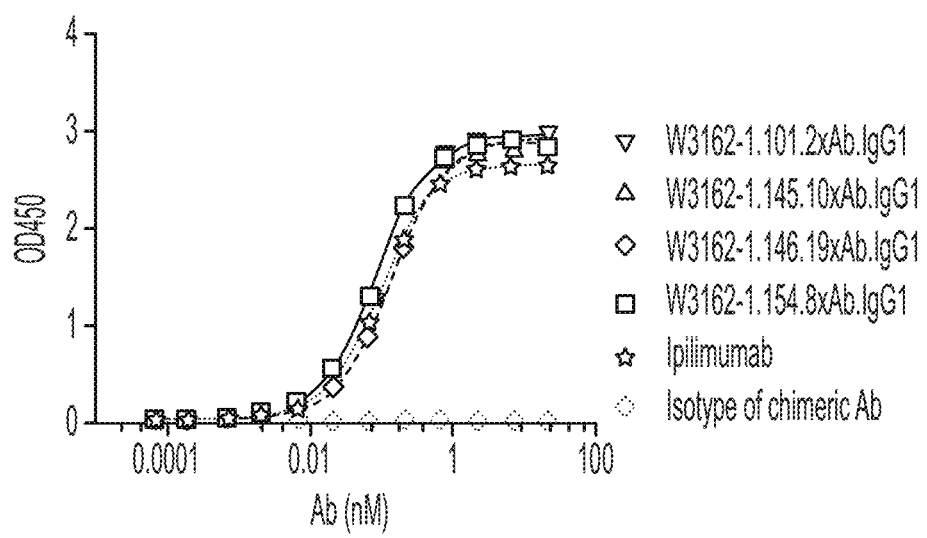
FIG. 2 shows graphs of chimeric antibodies binding to cyno CTLA-4 in ELISA.
Figure 3:
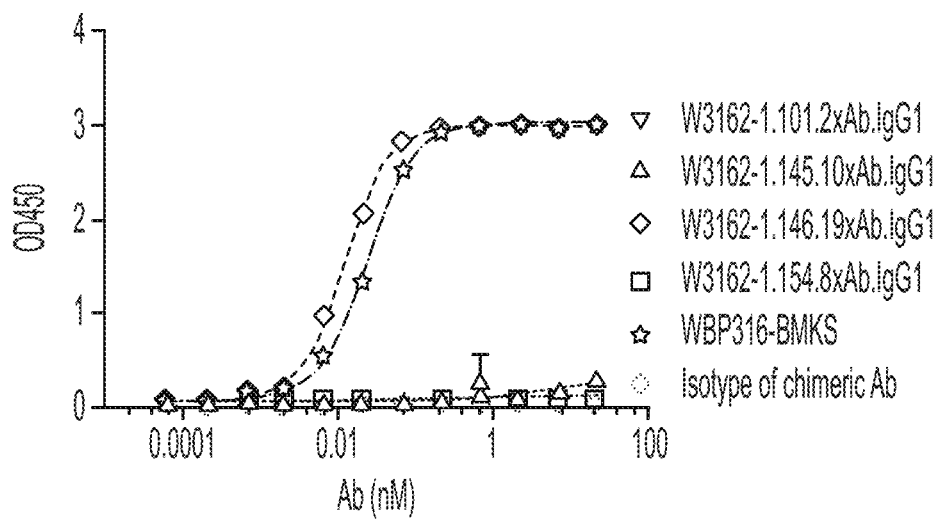
FIG. 3 shows graphs of chimeric antibodies binding to mouse CTLA-4 in ELISA.
Figure 4:
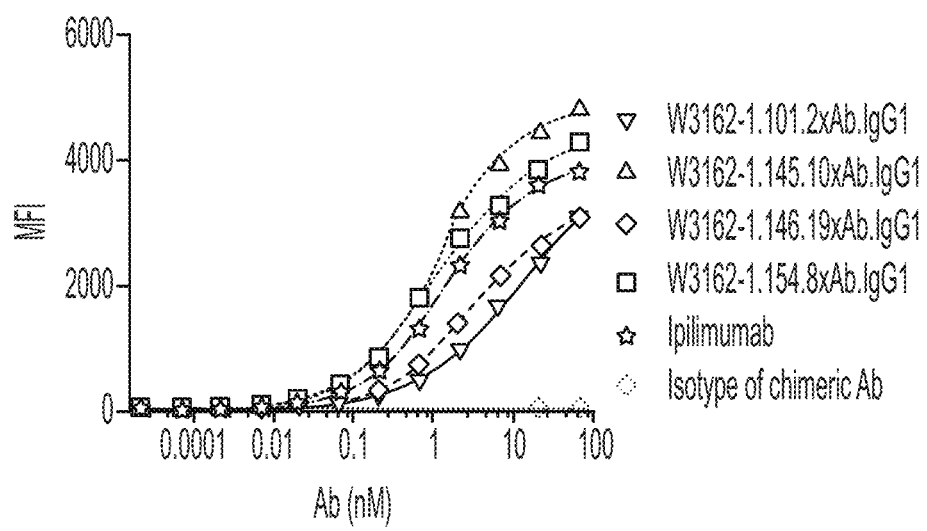
FIG. 4 shows graphs of chimeric antibodies binding to human CTLA-4 on cells by FACS.

The antibodies were tested on CTLA-4-binding ELISA. As shown in FIGS. 1, 2 and 3, all the four antibodies bound to human and monkey CTLA-4 with EC50 comparable to Ipilimumab (WBP316-BMK1), but only one antibody W3162-1.146.19 also bound to murine CTLA-4 at $EC_{50}$ of 0.01 nM. In order to confirm that the antibodies were able to bind CTLA-4 on cell surface, a CTLA-4-expressing cell line was used in FACS assays. These antibodies also bound to CTLA-4 on cell surface (FIG. 4) with $EC_{50}$ ranging from 1.14 nM to 9.42 nM. W3162-1.146.19 bounds to CTLA-4 on cell surface with $EC_{50}$ of 3.25 nM and W3162-1.154.8 bounds to CTLA-4 on cell surface with $EC_{50}$ of 1.26 nM.

The binding kinetics of four antibodies were measured using SPR. The antibodies were captured on immobilized goat anti-human Fc, and then human CTLA-4 ECD at different concentration was injected orderly. The sensorgrams for reference channel and buffer channel were subtracted from the test sensorgrams. The data was used to fit in 1:1 binding analysis. As show in the FIG. 5 and Table 4, all the four antibodies bound to human CTLA-4 ECD domain with higher affinity than Ipilimumab (WBP316-BMK1), with $K_D$ range of 2.08 E-09 nM to 6.80 E-11 nM.

TABLE 4

Kinetic of antibody binding on human CTLA-4 ECD

| Antibody | ka (1/Ms) | kd (1/s) | $K_D$ (M) |
|---|---|---|---|
| W3162-1.101.2 xAb.IgG1 | 6.95E+05 | 6.97E−05 | 1.00E−10 |
| W3162-1.145.10 xAb.IgG1 | 7.93E+06 | 1.65E−02 | 2.08E−09 |
| W3162-1.146.19 xAb.IgG1 | 7.09E+05 | 1.48E−04 | 2.08E−10 |
| W3162-1.154.8 xAb.IgG1 | 1.85E+06 | 1.25E−04 | 6.80E−11 |
| WBP316-BMK1 | 9.42E+05 | 3.46E−03 | 3.68E−09 |

2.2 Competition with Ligands of Chimeric Antibodies

Figure 6:
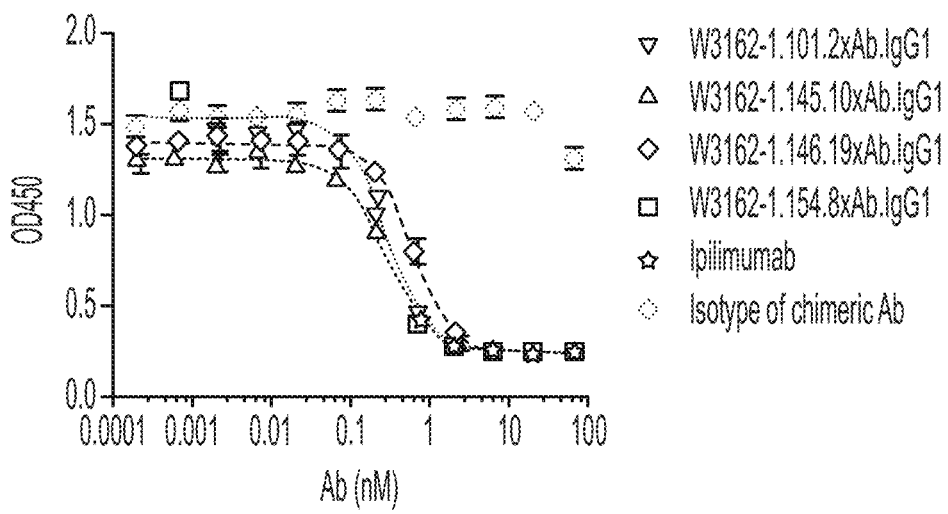
FIG. 6 shows the result of chimeric antibodies blocking ligand binding.
Figure 6:
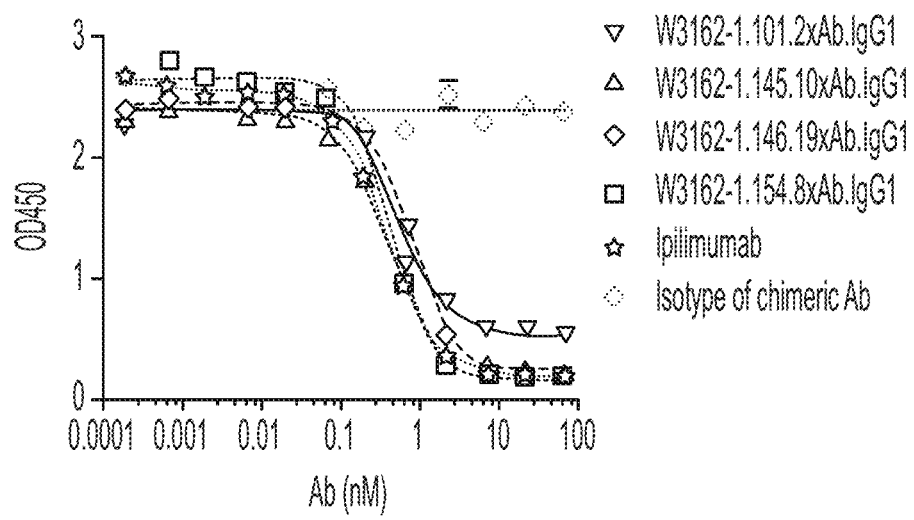
Figure 7:
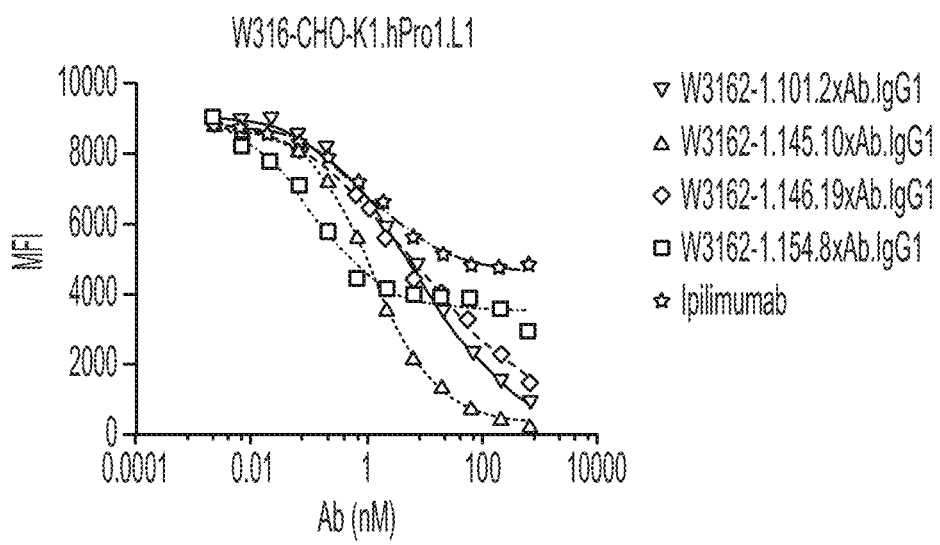
FIG. 7 shows graphs of chimeric Abs inhibited CTLA-4 binding on CD80- or CD86-expressing cells.
Figure 7:
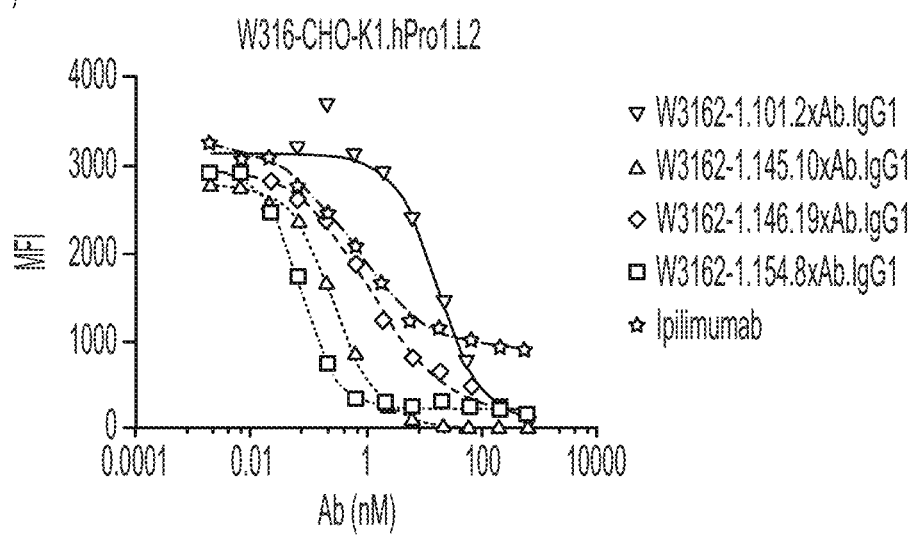

CTLA-4 was found binding to both CD80 and CD86 at 20 to 50 folds higher affinity than CD28 [Krummel 1996]. Therefore, the anti-CTLA-4 antibodies were tested whether they can compete with CD80 and CD86's binding on CTLA-4. Both ELISA and FACS were used as the competition assays. In ELISA based competition assay, human CTLA-4 was coated on the plates, and the antibodies mixed with biotinylated ligands were added into the plate. The bound ligands were detected by HRP conjugated streptavidin. As shown in FIGS. 6a and 6b, all four antibodies competed with ligands CD80 (B7-1, L1) and CD86 (B7-2, L2) in CTLA-4 binding, and three of them except W3162-1.101.2 had comparable $EC_{50}$ with Ipilimumab (WBP316-BMK1). In a FACS assay, the mixture of antibodies and biotinylated human CTLA-4 was added to CD80 or CD86 expressing cells, and the bound human CTLA-4 was detected by PE conjugated streptavidin. As shown in FIG. 7a (upper panel) and 7b (lower panel), all the four antibodies could effectively block CTLA-4's binding on the ligand-expressing cells. Three antibodies except W3162-1.154.8 could completely block CTLA-4 binding on CD80 cells, whereas Ipilimumab WBP316-BMK could only partially block this binding even at 200 nM, the highest concentration used (FIG. 7a). In the FACS assay of blocking CTLA-4 binding on CD86 cells (FIG. 7b), All of 4 antibodies could completely block CTLA-4 binding on CD86 cells, whereas Ipilimumab could only partially block this binding even at 200 nM, the highest concentration used. The kinetics of W3162-1.101.2 appeared differently: the blocking was less effective than Ipilimumab at low concentration and more effective than Ipilimumab at high concentration. Other three antibodies were more effective than Ipilimumab in blocking CTLA-4 at all the concentration tested.

2.3 Function in SEB Assay of Chimeric Antibodies

Figure 8:
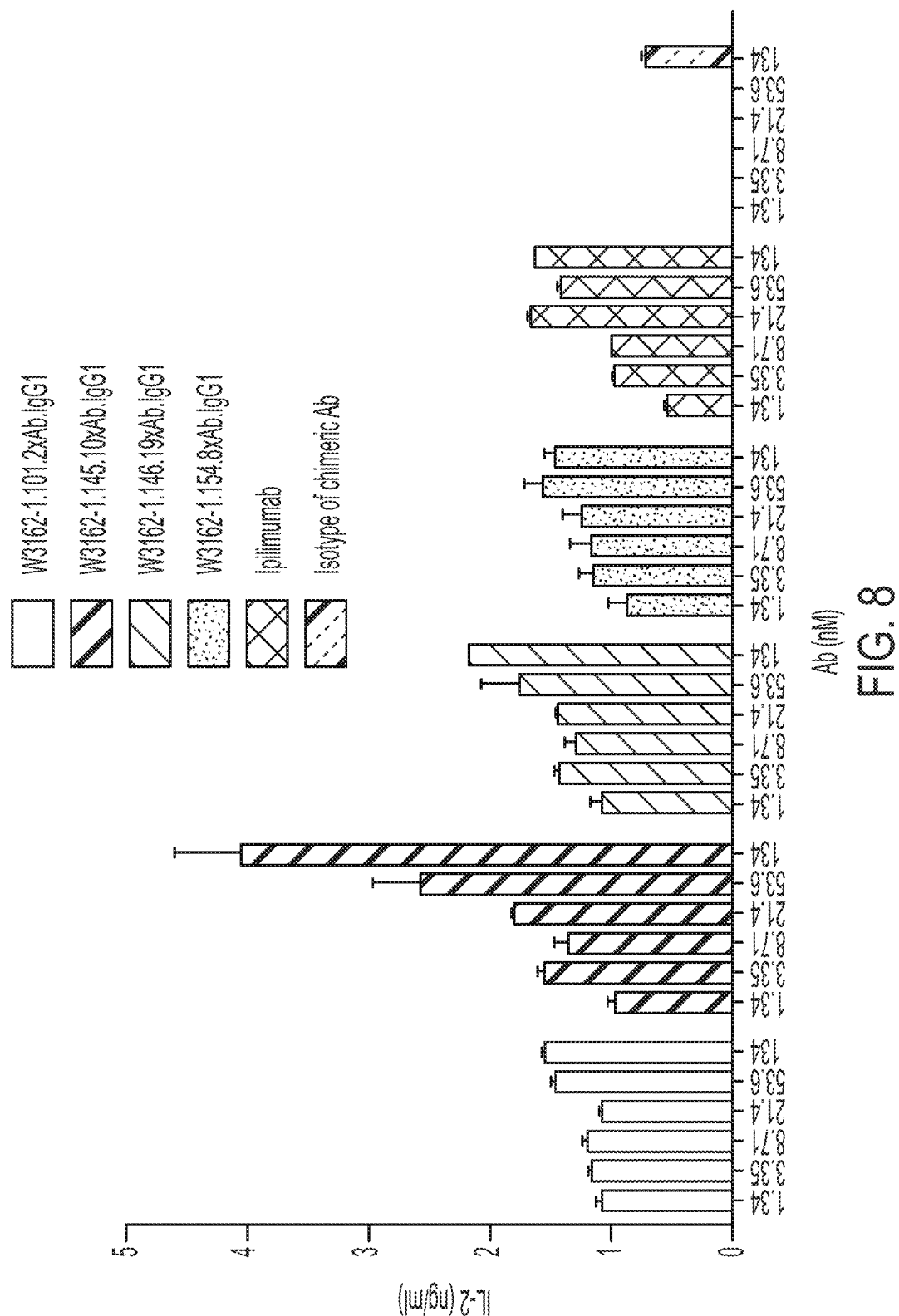
FIG. 8 shows the results of chimeric antibodies enhanced cytokine release from SEB stimulated PBMCs.

The function of anti-CTLA-4 antibodies with different concentration of 1.34 nM, 3.35 nM, 8.71 nM, 21.4 nM, 53.6 nM, 134 nM were tested in a modified T cell stimulation assay (SEB assay). Staphylococcal enterotoxin B (SEB) was used as a stimulator of human T cell activation, in which CTLA-4 was reported as an important player. The T cell activation was measured by secretion of IL-2. As shown in the FIG. 8, all the four antibodies promoted IL-2 secretion in a dose dependent manner, comparable with or superior to Ipilimumab.

Example 4: Characterization of Humanized Antibody

1. Humanization

"Best Fit" approach was used to humanize antibody light and heavy chains.

Three anti-CTLA-4 antibodies (except W3162-1.101.2 due to its relatively low binding activity in ELISA and FACS) were selected for humanization, using CDR-grafting technique. The CDRs (underlined in Table 5) and FRs of variable regions of the antibodies were defined using Kabat system. Based on the sequence homology and structural similarity, the gene of rat region FR1-3 was replaced by humanized region FR1-3, while region FR4 of the rat gene was replaced by humanized FR4 region derived from JH and JK genes that had the most similar structures. The hot spots of post-translational modification (PTM) of variable regions were modified to reduce the PTM risk. After verifying the template sequence and codon optimization, the heavy chain variable region and light chain variable region were synthesized and cloned into an expression vector, and then used for expression of the humanized antibodies. The humanized antibodies were purified using Protein A chromatography, and the kinetics binding on human, monkey and murine CTLA-4 were measured using SPR method.

TABLE 5

The variable region sequence of humanized anti-CTLA-4 antibodies

| Clone ID | | SEQ ID NO | Amino acid sequence |
|---|---|---|---|
| W3162-1.1 45.10-z7 | VH | 5 | EVQLVESGGGLVQPGGSLRLSCAAS<u>DLTFSNYDMA</u>WVRQAPGKGLEWVA <u>SISPSGGNTYYRDSVKG</u>RFTISRDNAKNSLYLQMNSLRAEDTAVYYCAR <u>HLWFAY</u>WGQGTLVTVSS |
| | VL | 12 | DIQMTQSPSSLSASVGDRVTITC<u>QASQDIGSNLI</u>WFQQKPGKAPKPMIY <u>YATHLAD</u>GVPSRFGSGSRSGTDYTLTISSLQPEDFATYYC<u>LQYKQYPRTF</u> GGGTKVEIK |
| W3162.1.14 6.19-z12 | VH | 6 | QVQLQESGPGLVKPSETLSLTCSVTYHTIT<u>SGYDWT</u>WIRKPPGKGMEWI GY<u>ISYSGNTNYNPSLKS</u>RVTISRDTSKNQFFLSLSSVTAADTAVYYCAS <u>MMVPHYYVMDA</u>WGQGTLVTVSS |
| | VL | 13 | DIVMTQTPLSLSVTPGQPASISC<u>RSSQSLLNSDGNTYLY</u>WYLQKPGQSP QLLIY<u>LVSKLGS</u>GVPNRFSGSGSGTDFTLKISRVEAEDVGVYYC<u>VQGTH DPWT</u>FGGGTKVEIK |

TABLE 5-continued

The variable region sequence of humanized anti-CTLA-4 antibodies

| Clone ID | | SEQ ID NO | Amino acid sequence |
|---|---|---|---|
| W3162.1.15VH 4.8-z35 | | 7 | QVQLVQSGAEVKKPGSSVKVSCKASGYTFT<u>NYFMN</u>WVRQAPGQGLEWMG <u>RVDPEQGRADYAEKFKK</u>RVTITADKSTSTAYMELSSLRSEDTAVYYCAR <u>RAMDNYGFAY</u>WGQGTLVTVSS |
| | VL | 14 | EIVLTQSPDFQSVTPKEKVTITC<u>SANSALSYMYW</u>YQQKPDQSPKLWVHG <u>TSNLAS</u>GVPSRFSGSGSGTDFTLTINSLEAEDAATYYC<u>HHWSNTQW</u>TFG GGTKVEIK |

TABLE 6

The variable region of humanized anti-CTLA-4 antibodies

| Clone ID | | SEQ ID NO | DNA sequence |
|---|---|---|---|
| W3162-1.145. 10-z7 | VH | 42 | GAGGTGCAGCTGGTGGAGAGCGGCGGAGGACTGGTGCAACCTGGCGGAAGC CTGAGACTGAGCTGCGCCGCCAGCGACCTGACCTTCAGCAACTACGACATG GCCTGGGTGAGACAGGCCCCTGGCAAGGGACTGGAGTGGGTGGCCAGCATC AGCCCCAGCGGCGGCAACACCTACTACAGGGACAGCGTGAAGGGCAGGTTC ACCATCAGCAGGGACAACGCCAAGAACAGCCTGTACCTGCAGATGAACAGC CTGAGGGCCGAGGACACCGCCGTGTACTACTGCGCCAGGCACCTGTGGTTC GCCTACTGGGGCCAGGGCACACTGGTGACCGTGAGCAGC |
| | VL | 45 | GACATCCAGATGACCCAGAGCCCTAGCAGCCTGAGCGCCAGCGTGGGGCGA TAGGGTGACCATCACCTGCCAGGCCAGCCAGGACATCGGCAGCAACCTGAT CTGGTTCCAGCAGAAGCCCGGCAAGGCCCCAAGCCTATGATCTACTACGC CACCCACCTGGCCGATGGCGTGCCTAGCAGATTCAGCGGCAGCAGAAGCGG CACCGACTACACCCTGACCATCAGCAGCCTGCAGCCCGAGGACTTCGCCAC CTACTACTGCCTGCAGTACAAGCAGTACCCCAGAACCTTCGGCGGCGGCAC CAAGGTGGAGATCAAG |
| W3162-1.146. 19-z12 | VH | 43 | CAGGTGCAGCTGCAGGAGAGCGGACCCGGACTGGTGAAGCCCTCCGAGACC CTGAGCCTGACCTGCAGCGTGACCTACCACACCATCACCAGCGGCTACGAC TGGACCTGGATCAGAAAGCCCCCCGGCAAAGGCATGGAGTGGATCGGCTAC ATCAGCTACAGCGGCAACACCAACTACAACCCCAGCCTGAAGAGCAGGGTG ACCATCAGCAGGGACACCAGCAAGAACCAGTTCTTCCTGAAGCTGAGCAGC GTGACAGCCGCCGATACCGCCGTGTACTACTGCGCCAGCATGATGGTGCCC CACTACTACGTGATGGACGCCTGGGGACAGGGCACCCTGGTGACAGTGAGC AGC |
| | VL | 46 | GACATCGTGATGACCCAGACCCCCCTGAGCCTGAGCGTGACACCTGGACAG CCCGCCAGCATCAGCTGCAGGTCCAGCCAGAGCCTGCTGAACAGCGACGGC AACACCTACCTGTACTGGTACCTGCAGAAGCCTGGCCAGAGCCCCCAGCTG CTGATCTACCTGGTGTCCAAGCTGGGCAGCGGCGTGCCTAACAGGTTTAGC GGCAGCGGCAGCGGCACCGATTTCACCCTGAAGATCAGCAGGGTGGAGGCC GAGGATGTGGGCGTGTACTACTGCGTGCAGGGCACCCACGATCCTTGGACC TTCGGCGGCGGAACCAAGGTGGAGATCAAG |
| W3162-1.154. 8-z35 | VH | 44 | CAGGTGCAGCTGGTGCAGAGCGGAGCCGAGGTGAAGAAGCCCGGCAGCAGC GTGAAGGTGAGCTGCAAGGCCAGCGGCTACACCTTCACCAACTACTTCATG AACTGGGTGAGGCAGGCCCCTGGACAAGGCCTGGAGTGGATGGGCAGAGTG GATCCCGAGCAGGGCAGGGCCGACTACGCCGAGAAGTTCAAGAAGAGGGTG ACCATCACCGCCGACAAGAGCACCAGCACCGCCTACATGGAGCTGAGCAGC CTGAGGAGCGAGGACACCGCCGTGTACTACTGCGCCAGGAGAGCCATGGAC AACTACGGCTTCGCCTACTGGGGCCAGGGAACCCTGGTGACCGTGAGCAGC |
| | VL | 47 | GAGATCGTGCTGACCCAGAGCCCCGACTTCCAGAGCGTGACCCCCAAGGAG AAGGTGACCATCACCTGCAGCGCCAACAGCGCCCTGAGCTACATGTACTGG TACCAGCAGAAGCCCGACCAGAGCCCCAAGCTGTGGGTGCACGGCACCAGC AATCTGGCCAGCGGCGTGCCTAGCAGATTTAGCGGCAGCGGCAGCGGCACC GATTTCACCCTGACCATCAACAGCCTGGAGGCCGAGGACGCCGCTACCTAC TACTGCCACCACTGGAGCAACACCCAGTGGACCTTCGGCGGCGGCACCAAG GTGGAGATCAAG |

2. Characterization of Humanized Antibodies 2.1 Antibodies Bound to Human, Monkey and Murine CTLA-4

2.1.1 CTLA-4-Binding ELISA

Humanized antibodies were expressed from mammalian cells and purified using Protein A affinity chromatography. Ipilimumab was from commercial source. Isotype control antibody, human CTLA-4 ECD with different tags (hFc or 6×His) and murine CTLA-4.ECD-hFc were prepared by WuXi Biologics. Murine CTLA-4.ECD-6×His and cynomolgus monkey CTLA-4 ECD-6×His were purchased from Sino Biological. HRP-conjugated goat anti-human IgG Fc was purchased from Bethyl (Cat: A80-304P).

ELISA was used to test binding of anti-human CTLA-4 antibodies to human, murine and cynomolgus monkey CTLA-4 protein. A 96-well plate was coated with human CTLA-4.ECD-6×His (1.0 µg/mL), cynomoguls monkey CTLA-4.ECD-6×His (0.5 µg/mL) or mouse CTLA-4.ECD-6×His (0.5 µg/mL) at 4° C. for 16-20 hours. After 1 hour blocking with 2% BSA in DBPS, testing antibodies, as well as positive and negative control antibodies were added to the plates and incubated at room temperature for 1 hour. The binding of the antibodies to the plates were detected by HRP-conjugated goat anti-human IgG antibody (1:5000 dilution) with 1 hour incubation. The color was developed by dispensing 100 μL of TMB substrate for 8 mins, and then stopped by 100 μL of 2N HCl. The absorbance at 450 nM was measured using a microplate spectrophotometer.

Figure 9:
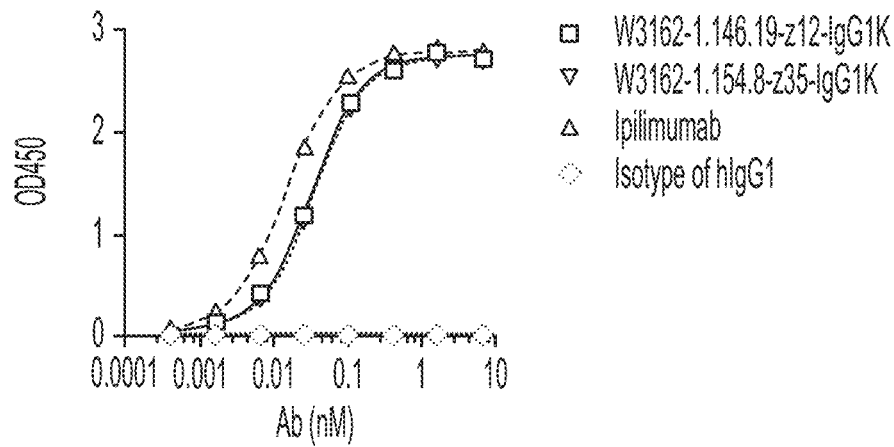
FIG. 9 shows graphs of humanized antibodies binding to human, cynomolgus monkey and mouse CTLA-4 in ELISA.
Figure 9:
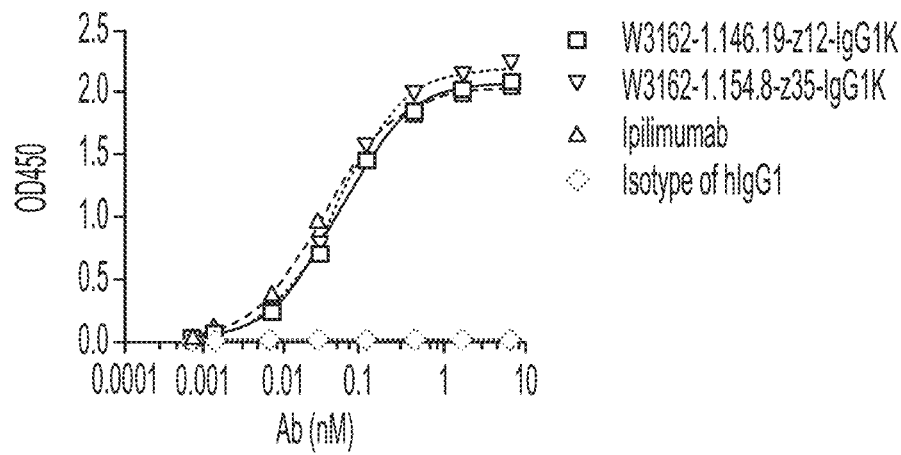
Figure 9:
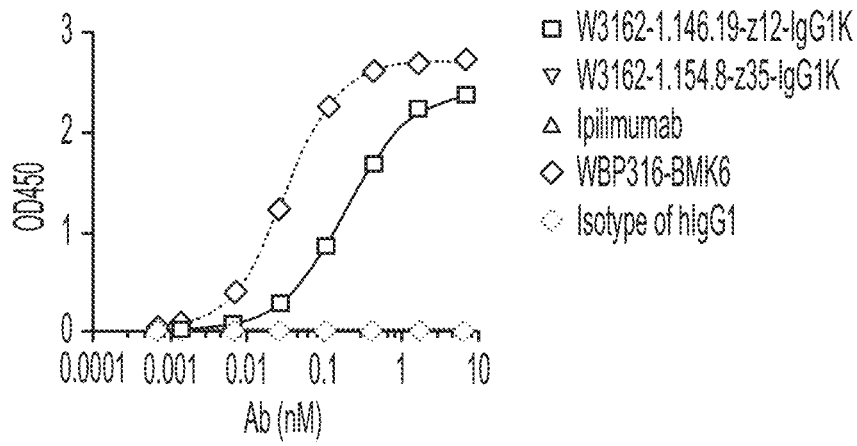

As shown in FIG. 9, the two antibodies W3162-1.146.19-z12-IgGk and W3162-1.154.8-z35-IgGk bound to human CTLA-4 with $EC_{50}$ of 0.03 nM and 0.04 nM, respectively, slightly higher than $EC_{50}$ of Ipilimumab (WBP316-BMK1) 0.01 nM (FIG. 9A). The two antibodies also bound to monkey CTLA-4 with $EC_{50}$ of 0.05 nM (FIG. 9B), but only W3162-1.146.19-z12-IgGk bound to murine CTLA-4 with $EC_{50}$ 0.19 nM. Neither W3162-1.154.8-z35-IgGk nor Ipilimumab bound to murine CTLA-4 (FIG. 9C).

2.1.2 CTLA-4-Binding FACS

Human CTLA4 expression 293F cell line was developed by WuXi Biologics.

PE conjugated goat anti-human IgG Fc fragment was purchased from Jackson (Catalog number 109-115-098). A number of $1\times10^5$ cells per well was added to each well of a 96-well plate and centrifuged at 1500 rpm for 4 minutes at 4° C. before removing the supernatant. Serial dilutions of test antibodies, positive and negative controls were added to the resuspended cells and incubated for 1 hour at 4° C. The cells were washed two times with 200 μL DPBS containing 1% BSA. PE conjugated goat anti-human IgG (1:100) diluted in DPBS containing 1% BSA was added to the cells and incubated at 4° C. for 1 hour. Additional washing steps were performed two times with 200 μL DPBS containing 1% BSA followed by centrifugation at 1500 rpm for 4 minutes at 4° C. Finally, the cells were resuspended in 100 μL DPBS containing 1% BSA and fluorescence values were measured by flow cytometry and analyzed by FlowJo.

Figure 10A:
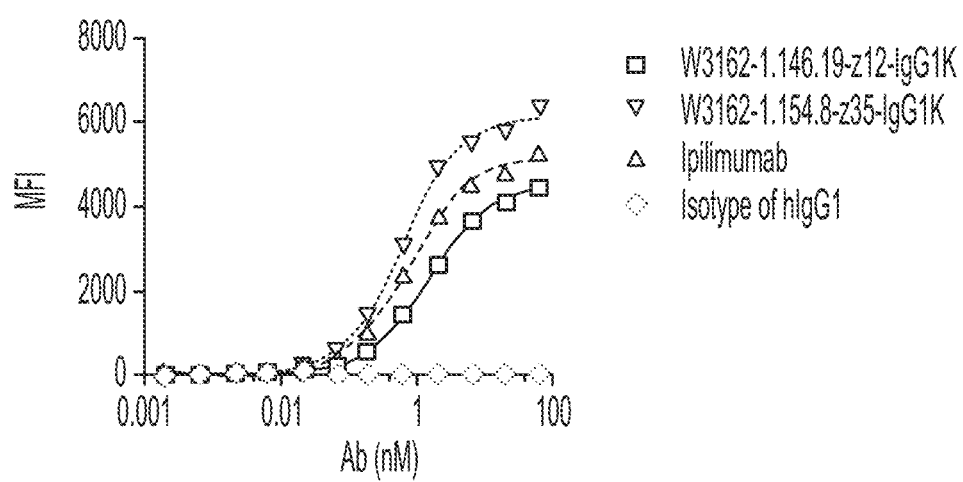
FIG. 10a shows graphs of humanized antibodies binding to CTLA-4 on cells (FACS).
Figure 10B:
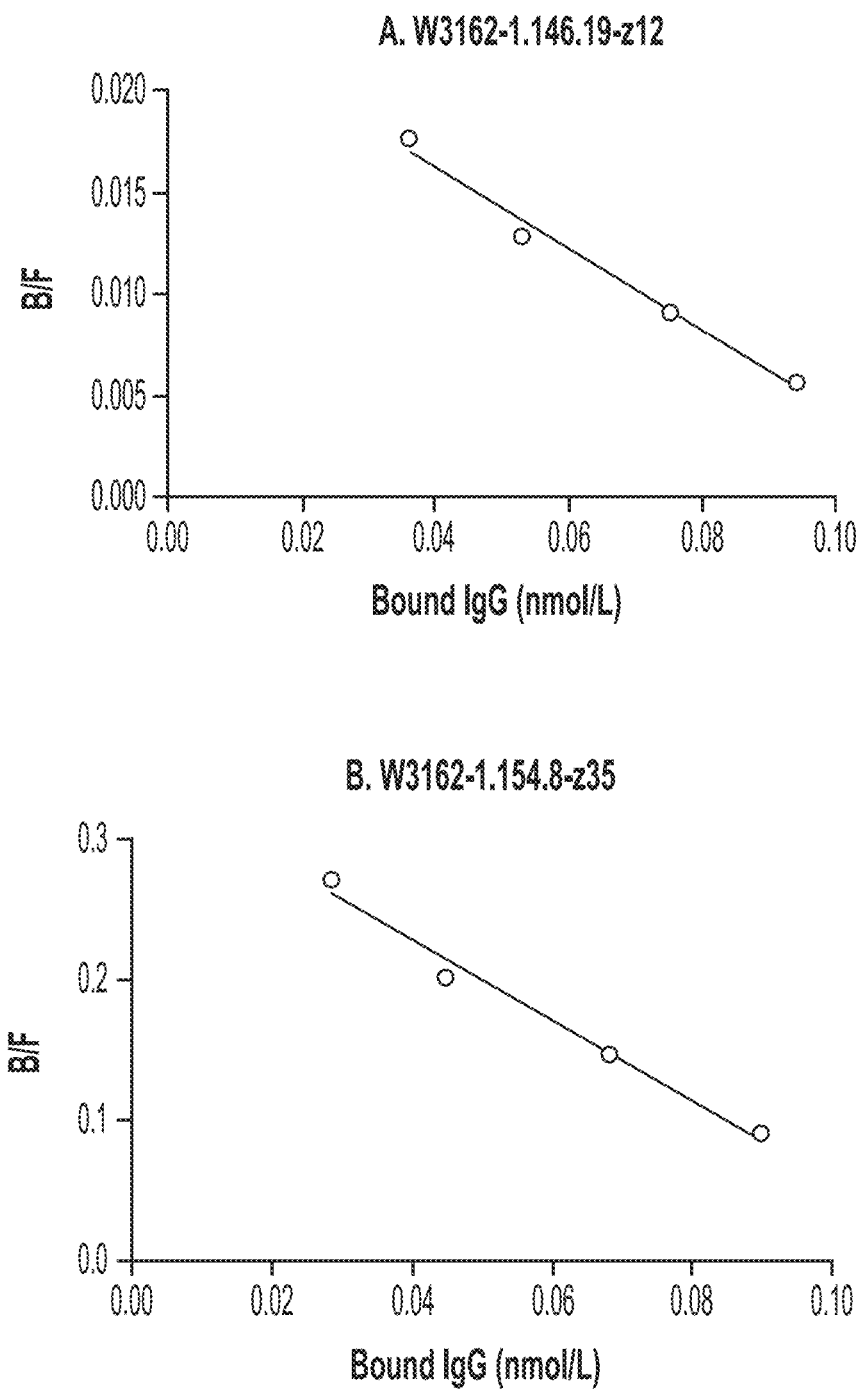
FIG. 10b shows graphs of affinity of humanized antibodies by FACS.
Figure 11:
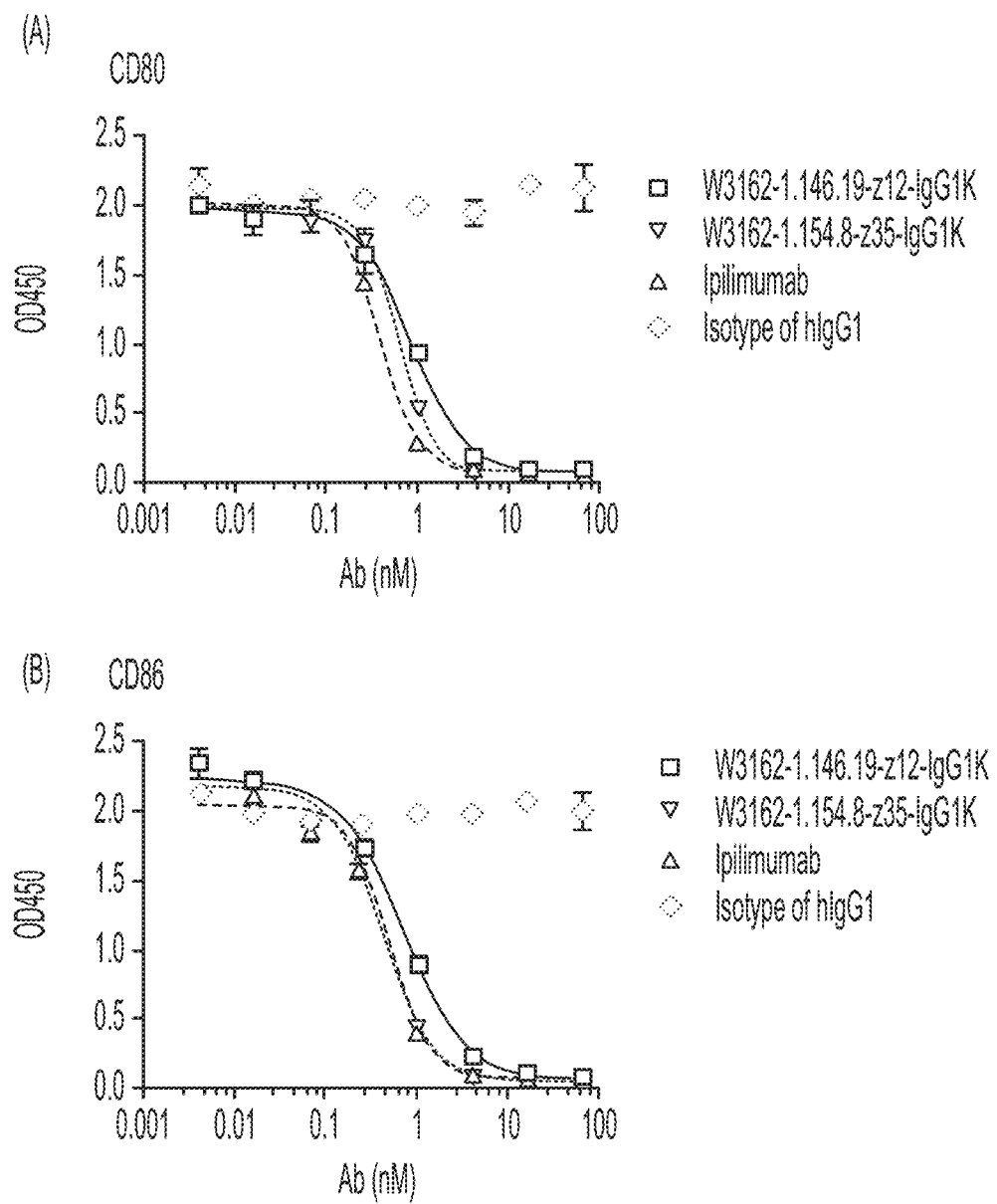
FIG. 11 shows that humanized antibodies block ligand binding by ELISA.

These antibodies were also able to bound human CTLA-4 on cell surface in FACS assay. As shown in FIG. 11 (FIG. 10a and FIG. 10b), W3162-1.146.19-z12-IgGk, W3162-1.154.8-z35-IgGk and Ipilimumab had slightly different $EC_{50}$ of 1.58 nM, 0.66 nM and 0.83 nM, respectively.

2.2 the Binding Kinetics of these Antibodies 2.2.1 the Binding Kinetics of these Antibodies were Measured Using SPR The experiment was to measure the on-rate constant (ka) and off-rate constant (kd) of the antibodies to CTLA-4 ECD based on SPR technology. The affinity constant ($K_D$) was consequently determined.

Biacore T200, Series S Sensor Chip CM5, Amine Coupling Kit, and 10×HBS-EP were purchased from GE Healthcare. Goat anti-human IgG Fc antibody was purchased from Jackson ImmunoResearch Lab (catalog number 109-005-098). In immobilization step, the activation buffer was prepared by mixing 400 mM EDC and 100 mM NHS immediately prior to injection. The CM5 sensor chip was activated for 420 s with the activation buffer. 30 μg/mL of goat anti-human IgG Fcγ antibody in 10 mM NaAc (pH 4.5) was then injected to Fc1-Fc4 channels for 200 s at a flow rate of 5 μL/min. The chip was deactivated by 1 M ethanolamine-HCl (GE). Then the antibodies were captured on the chip. Briefly, 4 μg/mL antibodies in running buffer (HBS-EP+) was injected individually to Fc3 channel for 30 s at a flow rate of 10 μL/min. Eight different concentrations (20 nM, 10 nM, 5 nM, 2.5 nM, 1.25 nM, 0.625 nM, 0.3125 nM and 0.15625 nM) of analyte CTLA-4 (WBP316.hCTLA-4.ECD-6×His) and blank running buffer were injected orderly to Fc1-Fc4 channels at a flow rate of 30 μL/min for an association phase of 120 s, followed by 2400 s dissociation phase. Regeneration buffer (10 mM Glycine pH 1.5) was injected at 10 μL/min for 30 s following every dissociation phase.

The binding kinetics of these antibodies were measured using SPR. The antibodies were captured on immobilized anti-human Fc and CTLA-4-ECD at different concentration was injected orderly. The sensorgrams for reference channel and buffer channel were subtracted from the test sensorgrams. The data was used for 1:1 binding analysis on human, monkey and mouse CTLA-4.ECD-6×His. As show in Table 7, humanized antibodies W3162-1.146.19-Z12, W145 and W3162-1.154.8-Z35 bound to human CTLA-4-ECD domain with affinity at 0.477 nM, 1.84 nM and 0.0968 nM, respectively. Comparing with rat antibodies, the humanized antibodies had comparable affinity. W3162-1.146.19-Z12 and W3162-1.154.8-Z35 have significantly higher affinity than Ipilimumab ($K_D$=3.68 nM). The antibody W3162-1.146.19-Z12 could also bind to murine CTLA-4, and its affinity before and after humanization is shown in Table 9. After humanization, its affinity 1.39 nM is slightly lower than affinity 0.906 nM of its parental antibody.

The affinity of W3162-1.146.19-Z12, W3162-1.145.10-z7 and W3162-1.154.8-Z35 binding to cynomolgus monkey CTLA-4-ECD was 1.92 nM, 0.598 nM, 0.131 nM, respectively (Table 8).

TABLE 7

Kinetic of antibody-binding on human CTLA-4 ECD

| Antibodies | ka (1/Ms) | kd (1/s) | $K_D$ (M) |
|---|---|---|---|
| W3162-1.146.19-z12-uAb.IgG1K | 2.06E+05 | 9.82E−05 | 4.77E−10 |
| W3162-1.146.19 xAb.IgG1 | 7.09E+05 | 1.48E−04 | 2.08E−10 |
| W3162_1.145.10-z7-uAb.IgG1K | 7.37E+06 | 1.35E−02 | 1.84E−09 |
| W3162-1.145.10 xAb.IgG1 | 7.93E+06 | 1.65E−02 | 2.08E−09 |
| W3162_1.154.8-z35-uAb.IgG1K | 1.23E+06 | 1.19E−04 | 9.68E−11 |
| W3162-1.154.8 xAb.IgG1 | 1.85E+06 | 1.25E−04 | 6.80E−11 |
| Ipilimumab | 9.42E+05 | 3.46E−03 | 3.68E−09 |

TABLE 8

Kinetic of antibody-binding on monkey CTLA-4 ECD

| Antibodies | ka (1/Ms) | kd (1/s) | $K_D$ (M) |
|---|---|---|---|
| W3162-1.146.19-z12-uAb.IgG1K | 1.73E+05 | 3.31E−04 | 1.92E−09 |
| W3162-1.146.19 xAb.IgG1 | 2.91E+05 | 1.07E−04 | 3.69E−10 |
| W3162_1.145.10-z7-uAb.IgG1K | 4.52E+06 | 2.71E−03 | 5.98E−10 |
| W3162-1.145.10 xAb.IgG1 | 1.06E+07 | 3.77E−03 | 3.55E−10 |
| W3162_1.154.8-z35-uAb.IgG1K | 9.32E+05 | 1.22E−04 | 1.31E−10 |
| W3162-1.154.8 xAb.IgG1 | 1.25E+06 | 1.09E−04 | 8.72E−11 |

TABLE 9

Kinetic of antibody-binding on mouse CTLA-4 ECD

| Antibodies | ka (1/Ms) | kd (1/s) | $K_D$ (M) |
|---|---|---|---|
| W3162-1.146.19-z8-uAb.IgG1K | 1.72E+05 | 2.39E−04 | 1.39E−09 |
| W3162-1.146.19 xAb.IgG1 | 2.51E+05 | 2.28E−04 | 9.06E−10 |

2.2.2 Affinity Test by FACS

FITC conjugated goat anti-human IgG Fc was purchased from Jackson Immunoresearch Lab (catalog number 109-095-098), and BD CantoII was used for this assay. Briefly, HEK293 cells expressing human CTLA-4 were transferred in to 96-well U-bottom plates (BD) at a density of $5\times10^4$ cells/well. Testing antibodies were 1:2-fold serially diluted in PBS with 1% BSA and incubated with cells at 4° C. for 1 hour. After centrifugation at 1500 rpm for 4 min, the supernatant was discarded. The secondary antibody, FITC conjugated goat anti-human IgG Fc (3.2 FITC per IgG, Jackson Immunoresearch Lab), was added to re-suspend cells to final concentration 14 μg/ml, and incubated at 4° C. in the dark for 30 min. The cells were then washed once and re-suspended in PBS with 1% BSA, and analyzed by flow cytometry (BD). Fluorescence intensity was converted to bound molecules/cell based on the quantitative beads (Quantum™ MESF Kits, Bangs Laboratories). $K_D$ was calculated using Graphpad Prism5.

Figure 5:
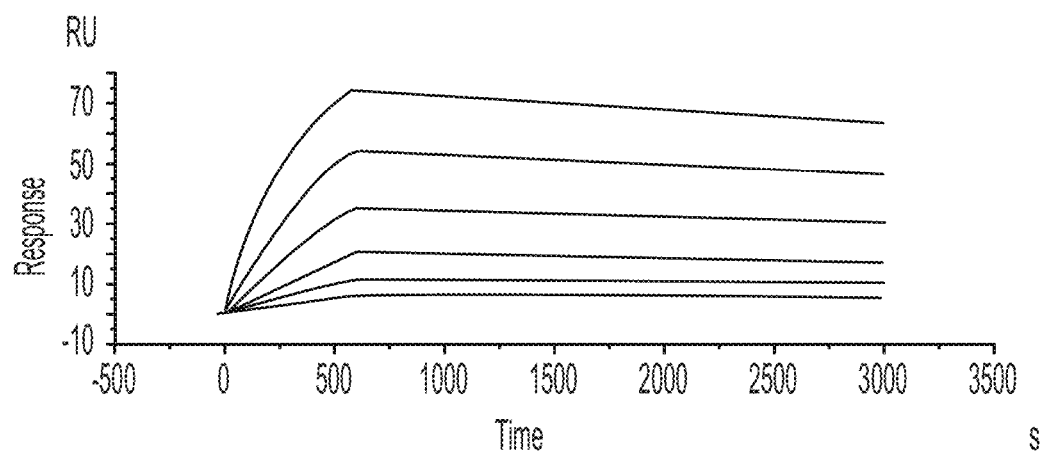
FIG. 5 shows the result of chimeric antibodies binding on human CTLA-4 by SPR.
Figure 5:
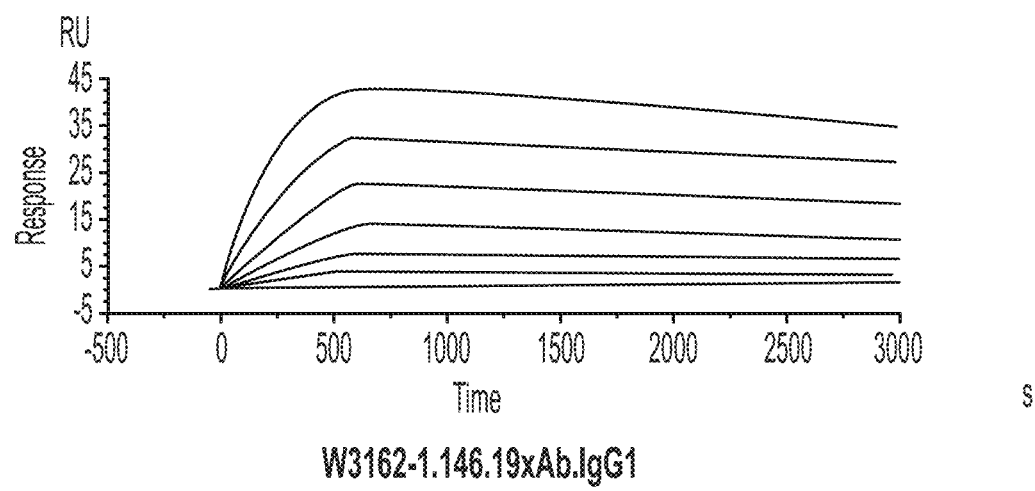
Figure 5:
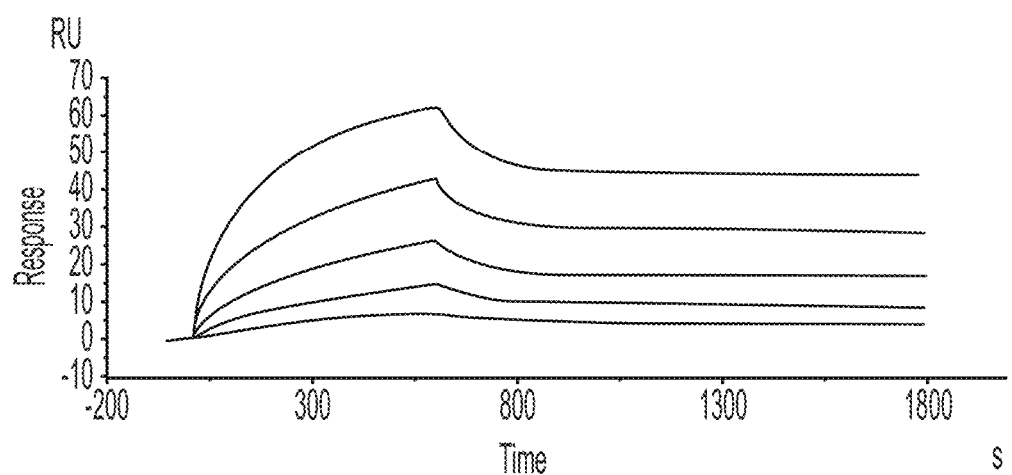
Figure 5:
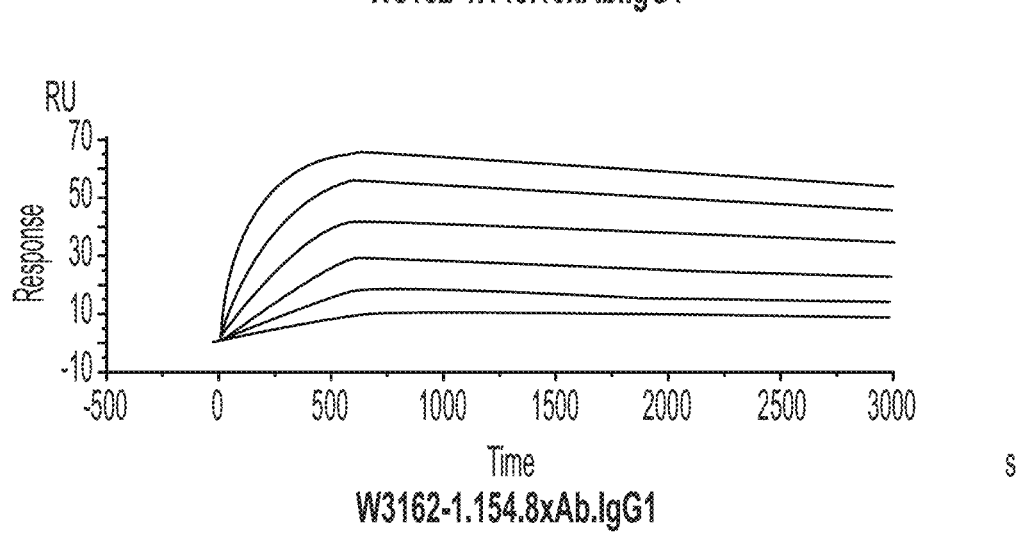
Figure 5:
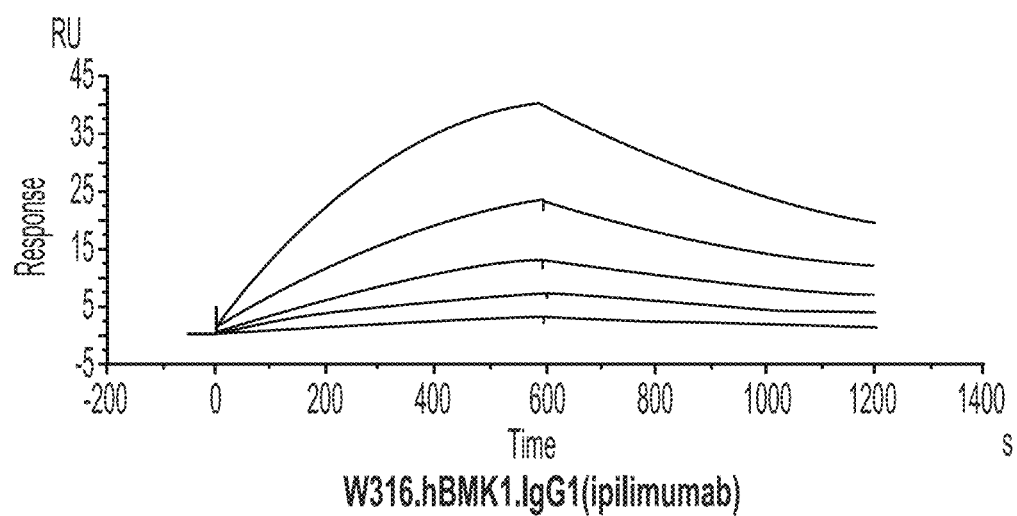

The affinity of humanized antibodies binding to cell surface CTLA-4 was measured by flow cytometry method, modified from Benedict's method [Benedict 1997 JIM]. After measure fluoresce of antibodies binding to CTLA-4-expressing CHO cells, the bound antibody and free antibody were analyzed and fitted to the equation, as shown in FIG. 5. Based on the data and formula, calculated affinity constant $K_D$ is shown in the Table 10. Affinity of humanized antibody W3162-1.146.19-Z12 and W3162-1.154.8-Z35 had high affinity at 5.05 and 0.35 nM, respectively, whereas the affinity of Ipilimumab is 0.97 nM.

TABLE 10

Affinity test by FACS

| Sample | $K_D$ (M) | Bmax | $R^2$ |
|---|---|---|---|
| W3162-1.146.19-z12-IgG1K | 5.0E−09 | 1.2E−10 | 0.99 |
| W3162-1.154.8-z35-IgG1K | 3.5E−10 | 1.2E−10 | 0.98 |
| Ipilimumab | 9.7E−10 | 7.2E−11 | 0.99 |

2.3 Competition with Ligands

In order to test whether the humanized antibodies maintained its ability of blocking CTLA-4 binding on CD80 and CD86, both ELISA and FACS were used in competition assay. Two CTLA-4 ligands CD80 and CD86 were purchased from Sino Biological (Catalog number 10698-H08H and 10699-H08H). Biotinylated anti-His tag antibody was purchased from Genscript (Catalog number A00613). HRP conjugated streptavidin was purchased from Invitrogen (Catalog number SNN1004).

2.3.1 the ELISA-Based Competition Assay

ELISA was used to test whether the antibodies could inhibit the binding of human CTLA-4 to its ligands human CD80 and CD86. Plates were coated with human CTLA-4.ECD.hFc (0.5 μg/mL) at 4° C. for 16-20 hours. After 1 hour blocking with 2% BSA in DBPS, testing antibodies, as well as positive and negative control antibodies were pre-mixed with 0.25 μg/mL of CD80-6×His or CD86-6×His, and then added to the plates and incubated at room temperature for 1 hour. After washing three times with PBS containing 0.05% Tween 20, biotinylated anti-His tag antibody was 1:2000 diluted and added. The plates were incubated at room temperature for 1 hour. The bound ligands were detected by HRP conjugated streptavidin (1:20000). The color was developed by dispensing 100 μL of TMB substrate for 8 mins, and then stopped by 100 μL of 2N HCl. The absorbance at 450 nM was measured using a microplate spectrophotometer.

As shown in FIG. 11, W3162-1.146.19-z12-IgGk and W3162-1.154.8-z35-IgGk had similar effect as Ipilimumab in blocking ligands binding with coated CTLA-4, with $IC_{50}$ of 0.87 nM, 0.63 nM and 0.40 nM for CD80, and 0.71 nM, 0.50 nM and 0.42 nM for CD86.

2.3.2 the FACS Assay

To test whether the antibodies could block CTLA-4 binding to CD80 and CD86 on cell surface, we used FACS to test this competition. The CD80- and CD86-expressing CHO cell lines were developed by WuXi Biologics. Biotinylated CTLA-4.ECD.hFc was made by WuXi Biologics. PE conjugated Streptavidin was purchased from eBioscience (Catalog number 12-4317).

CD80- or CD86-expressing cells were added to each well of a 96-well plate at 1×10⁵ per well and centrifuged at 1500 rpm for 4 minutes at 4° C. before removing the supernatant. Serial dilutions of test antibodies, positive and negative controls were mixed with biotinylated human CTLA4.ECD.hFc. Due to different density of ligands on cell surface, 0.02 μg/mL of hCTLA-4.ECD.hFc-Biotin was used for human CD80 cells and 0.08 μg/mL of hCTLA-4.ECD.hFc-Biotin for human CD86 cells. Then the mixtures of antibody and CTLA-4 were added to the cells and incubated for 1 hour at 4° C. The cells were washed two times with 200 μL FACS buffer (DPBS containing 1% BSA). Streptavidin PE 1 to 333 diluted in FACS buffer was added to the cells and incubated at 4° C. for 1 hour. Additional washing steps were performed two times with 200 μL FACS buffer followed by centrifugation at 1500 rpm for 4 minutes at 4° C. Finally, the cells were resuspended in 100 μL FACS buffer and fluorescence values were measured by flow cytometry and analyzed by FlowJo.

Figure 12:
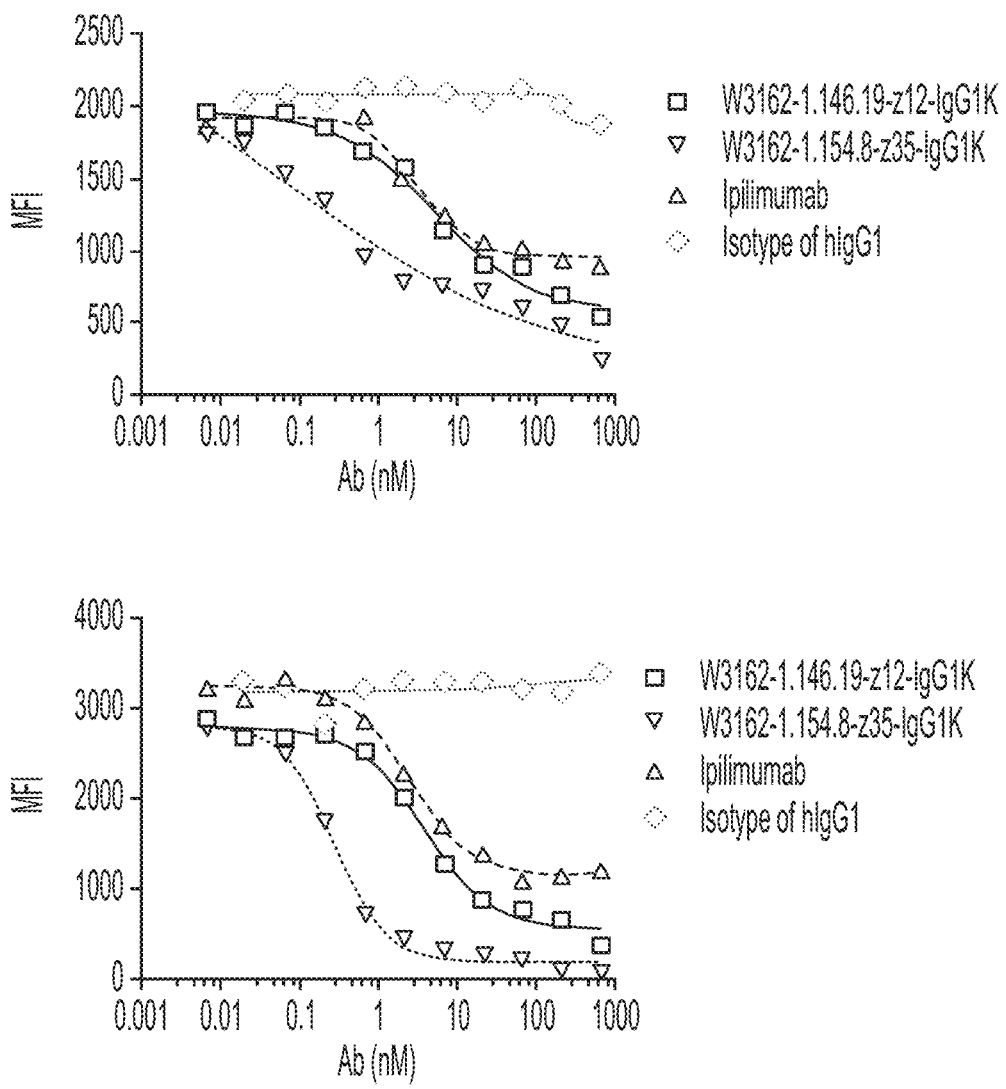
FIG. 12 shows that humanized antibodies block CTLA-4 binding to its ligands by FACS.

The results are shown in FIG. 12. The two humanized antibodies could more effectively block CTLA-4/ligand binding than Ipilimumab. At the highest concentration used, Ipilimumab only blocked 32% CTLA-4 binding to CD80 and 40% of CTLA-4 binding to CD86. In comparison, antibody W3162-1.146.19-Z12 blocked 71% of CTLA-4 binding on CD80 and 73% of CTLA-4 binding on CD86, and antibody W3162-1.154.8-Z35 blocked 89% of CTLA-4 binding on CD80 and 98% of CTLA-4 binding on CD86. $IC_{50}$ of Ipilimumab, W3162-1.146.19-Z12 and W3162-1.154.8-Z35 directing against CD80 were 3.23, 6.60 and 0.07 nM respectively. $IC_{50}$ of Ipilimumab, W3162-1.146.19-Z12 and W3162-1.154.8-Z35 directing against CD86 were 2.52, 5.15 and 0.28 nM respectively.

2.4 Cytokine Release of SEB Stimulated PBMCs

Anti-CTLA4 antibodies were tested whether they could enhance cytokines release of human PBMC after SEB (from The Second Military Medical University) stimulation. Peripheral blood from healthy donors was obtained and cells were isolated by Ficoll GE Healthcare, 17-1440-02) density gradient centrifugation. After the buoyant layer was removed, the platelets were removed by several washes with medium. A number of 1×10⁵ human PBMC cells were added to each well of a 96-well plate. Serial dilutions of test antibodies, positive and negative controls were mixed with SEB (10 ng/mL), and then added to the pelleted cells and incubated for 3 days at 37° C. The supernatants were collected to measure human IL-2 concentration.

For human IL-2 test, plates were pre-coated with 1.0 μg/ml human IL-2 antibody (R&D System MAB602) at 4° C. for 16-20 hours. After 1 hour blocking with 2% BSA (BovoGen) in DBPS, the supernatants containing IL-2 were added to the plates and incubated at room temperature for 2 hours. After washing three times with PBST (containing 0.05% Tween 20), biotinylated human IL-2 antibody (R&D system, BAF202) was diluted and added at concentration of 0.5 g/mL. The plates were incubated at room temperature for 1 hour. The bound biotinylated antibody was detected by 1:20000 diluted streptavidin conjugated HRP (Invitrogen, SNN1004). After 1 hour incubation, the color was developed by dispensing 100 µL of TMB substrate, and then stopped by 100 µL of 2M HCl. The absorbance at 450 nm and 540 nm was measured using a microplate spectrophotometer.

Figure 13:
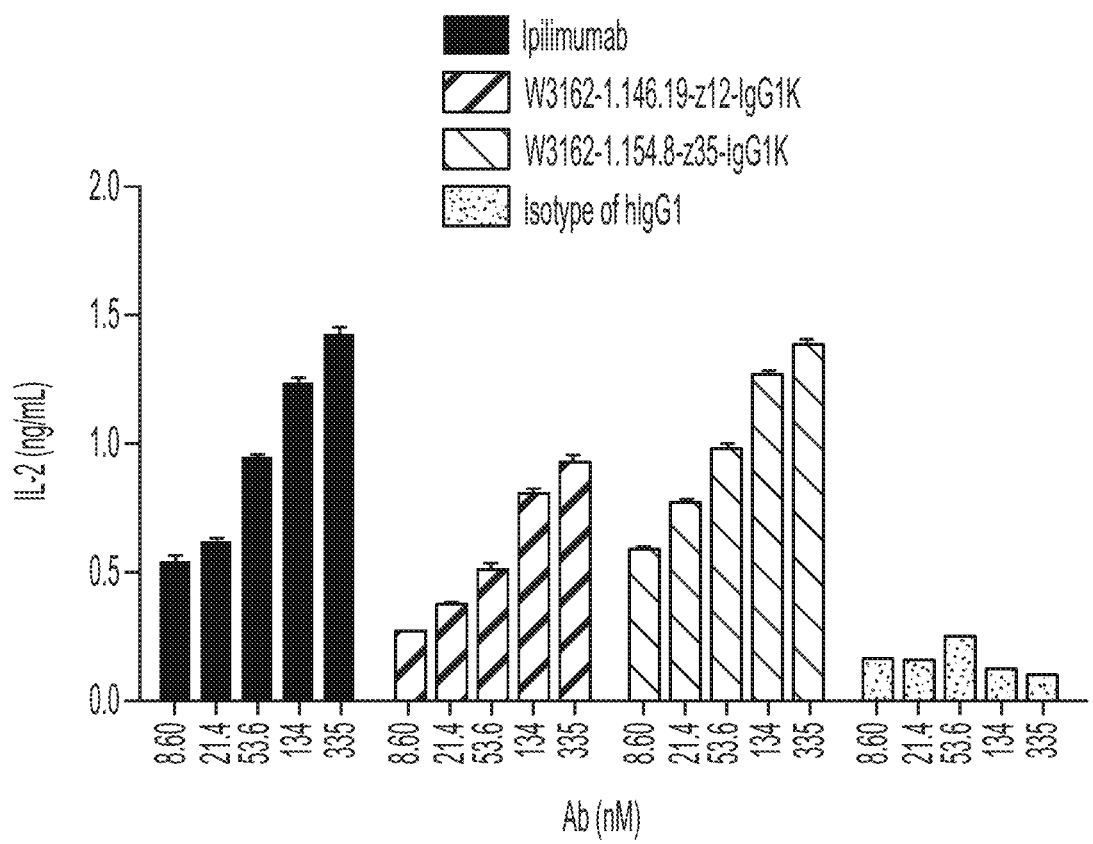
FIG. 13 shows that humanized antibodies enhance cytokine release in SEB assay.
Figure 14A:
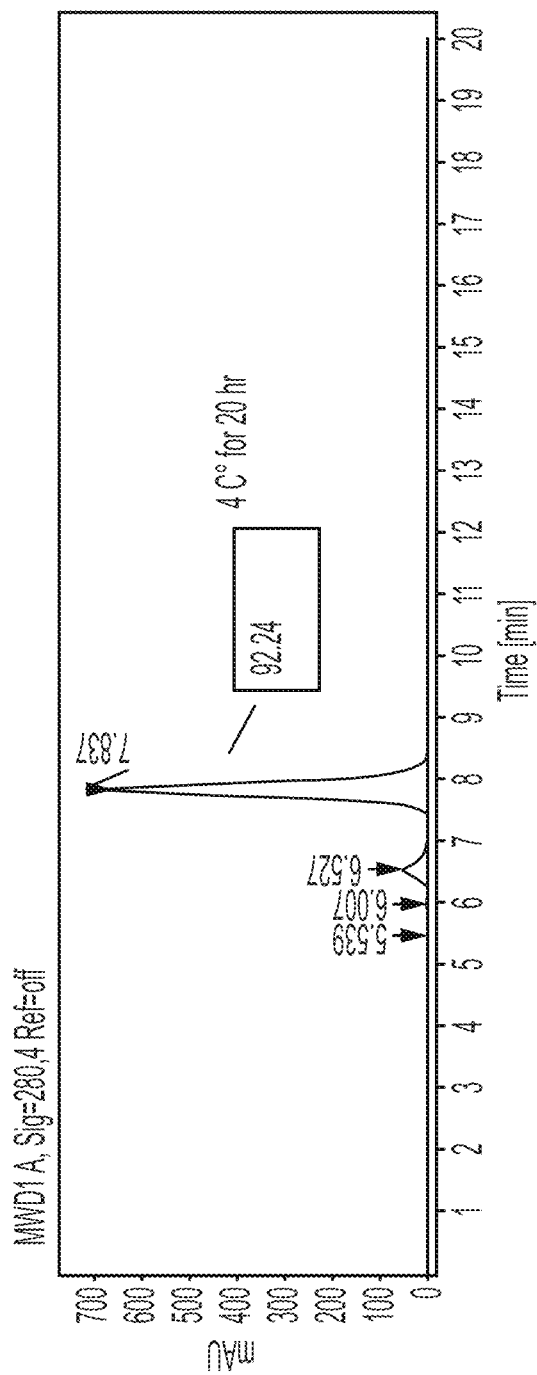
FIG. 14 shows the SEC profile of W3162-1.146.19-Z12 or W3162-1.154.8-Z35 at different conditions.
Figure 14B:
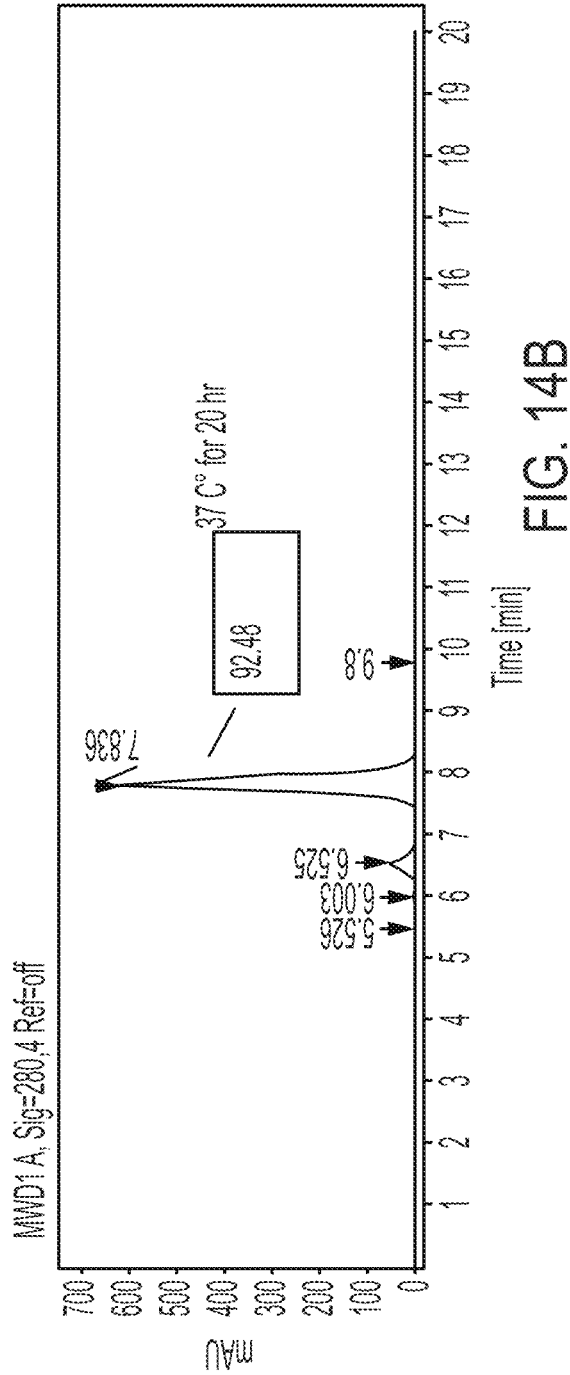
Figure 14C:
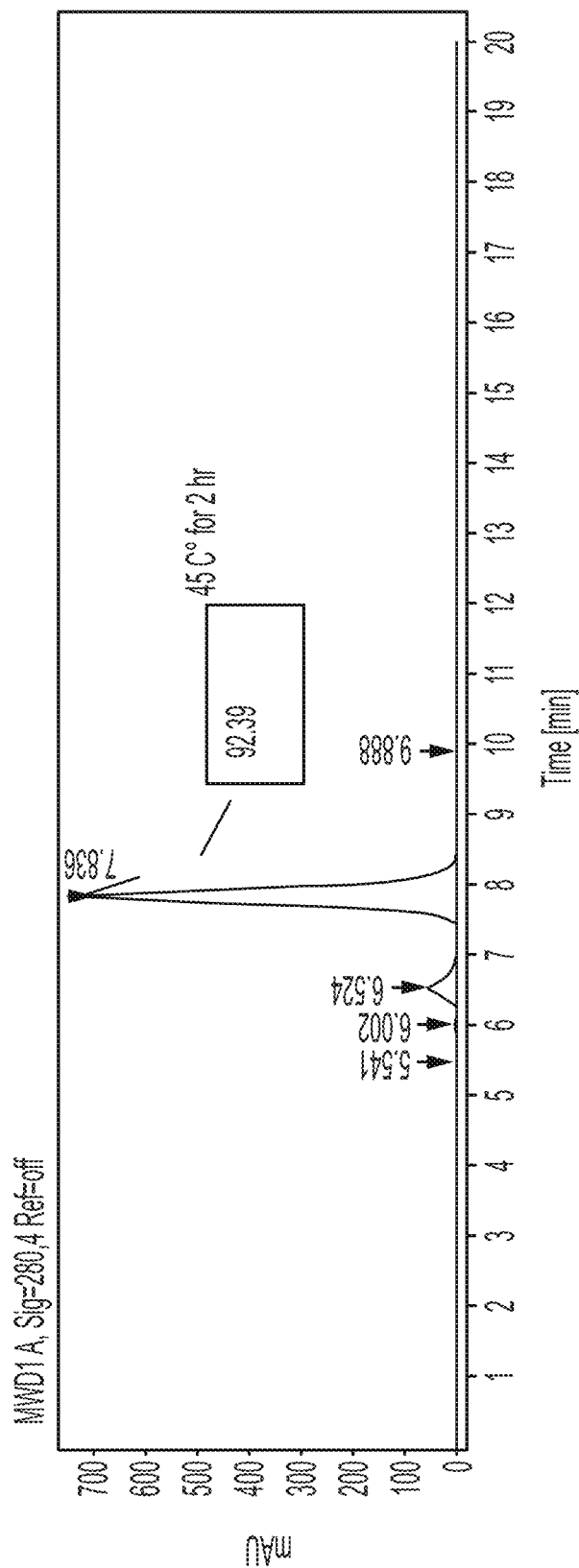
Figure 14D:
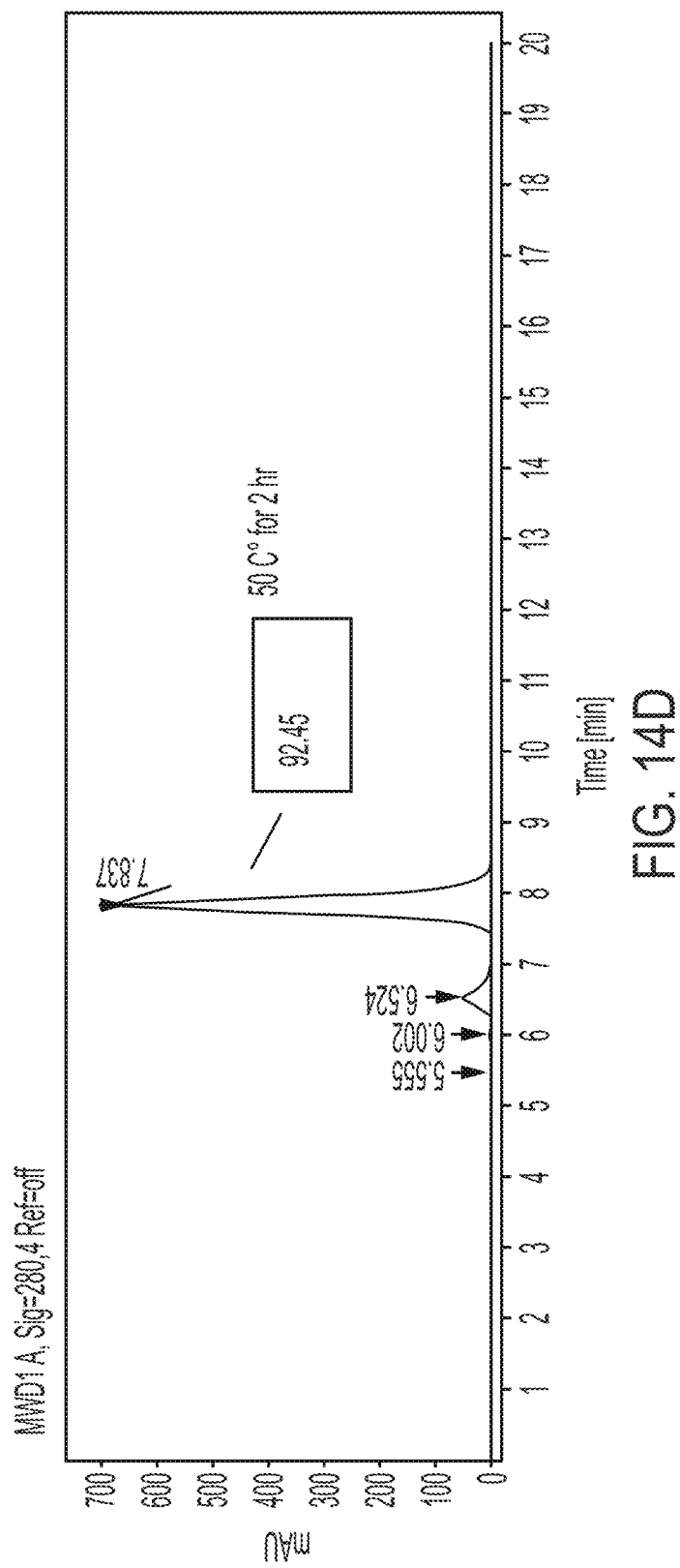
Figure 14E:
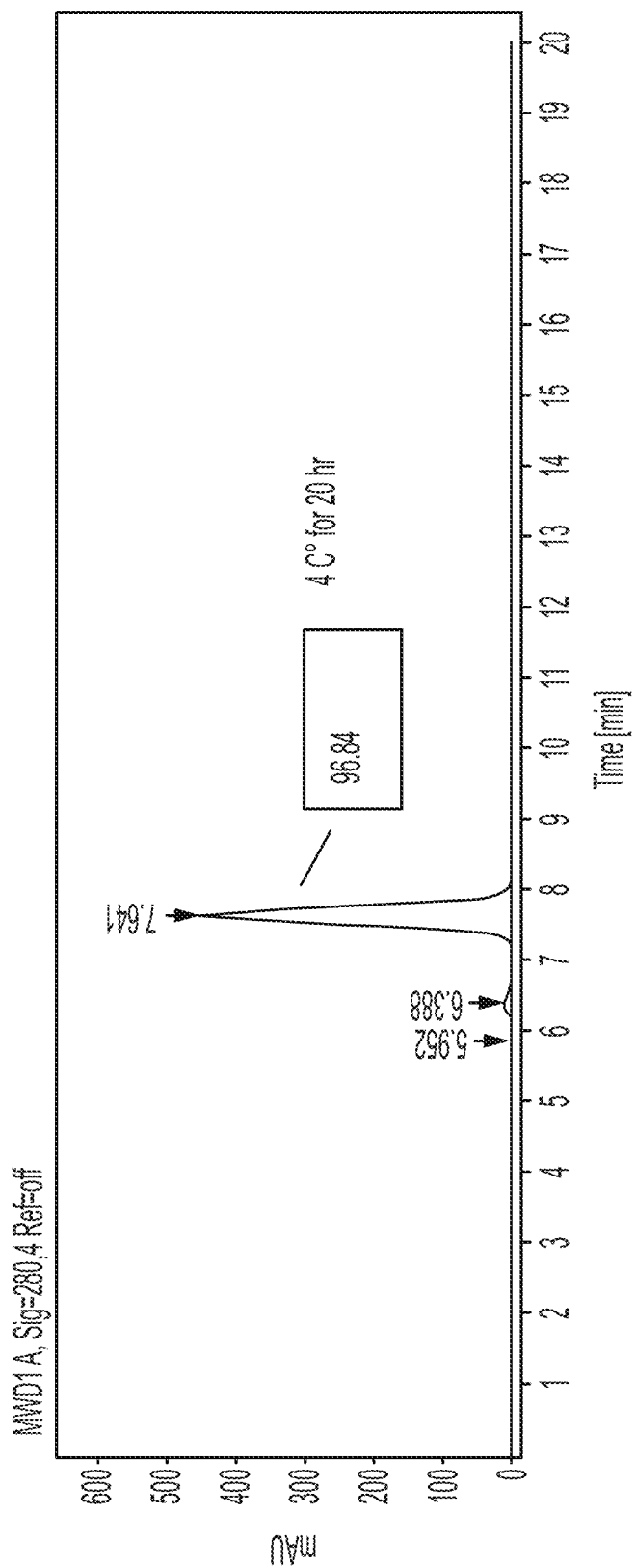
Figure 14F:
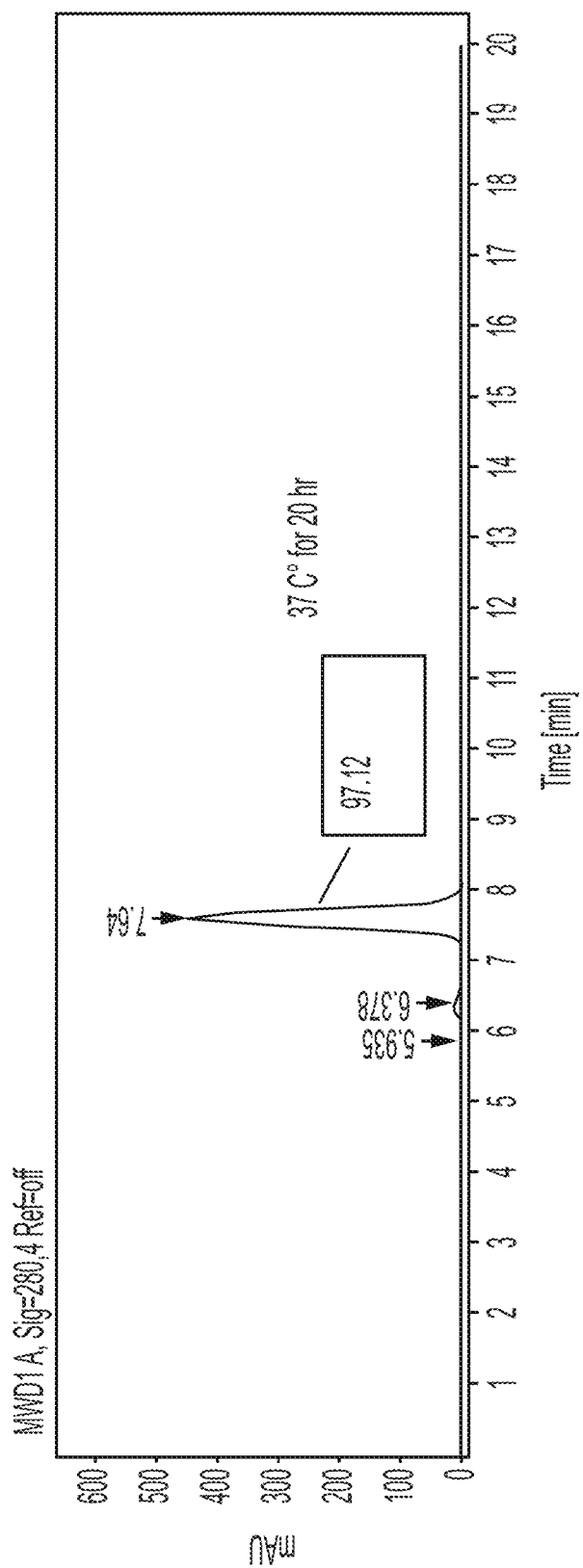
Figure 14G:
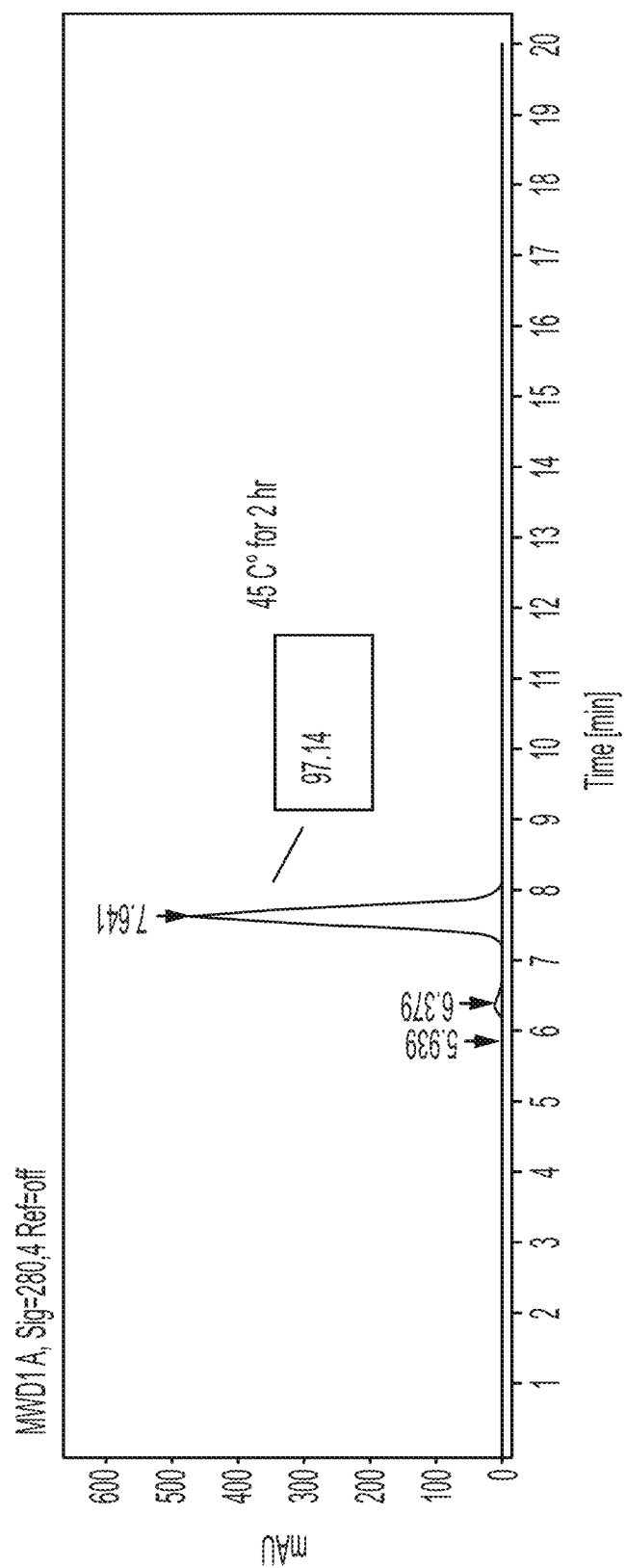
Figure 14H:
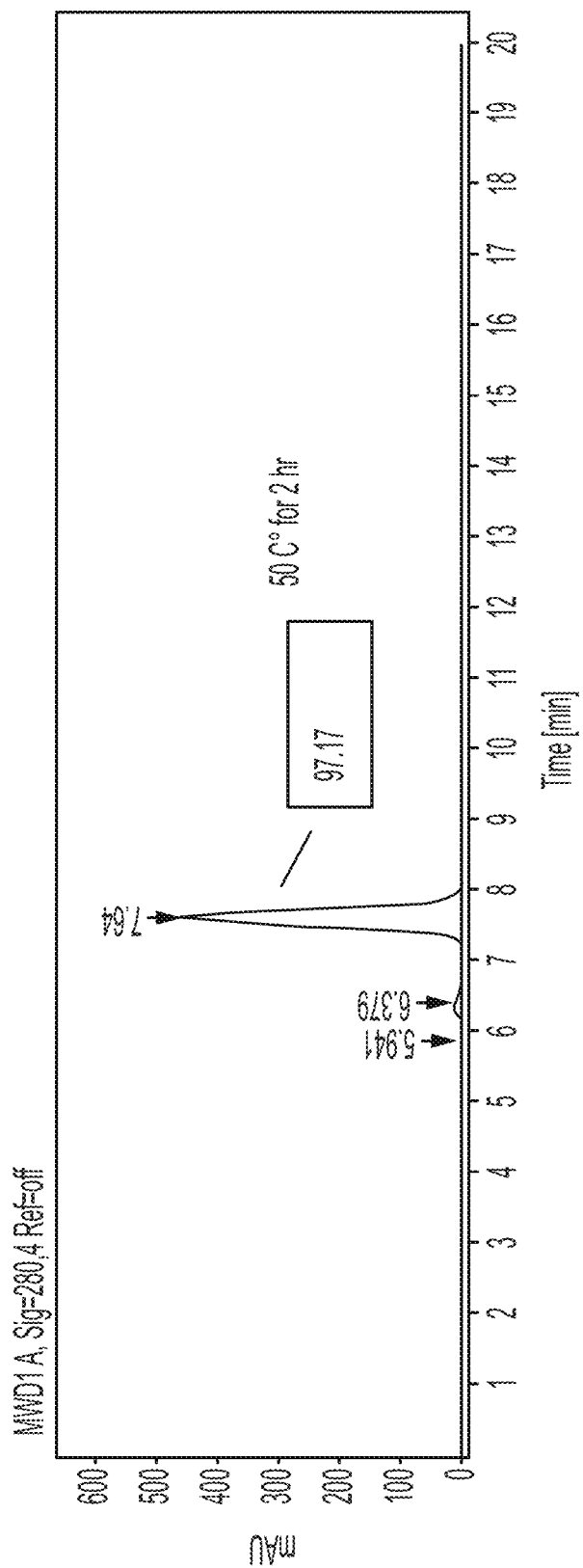

In a cell-based assay, the humanized antibodies (8.60 nM, 21.4 nM, 53.6 nM, 134 nM, 335 nM) were tested whether they could enhance superantigen SEB stimulated human PBMCs. After 3 days stimulation, IL-2 from the PBMC was measure using ELISA. Compared with an isotype control antibody, both the two humanized antibodies (W3162-1.146.19-Z12, W3162-1.154.8-Z35) and Ipilimumab could enhance IL-2 release from the PBMCs in a dose-dependent manner (FIG. 13).

2.5 Thermostability

The stability of the lead antibodies was tested at different temperature. Briefly, 100 µL each antibody sample was pipetted into individual tubes, and the samples were incubated at 4° C. or 37° C. for 20 hours, or 45° C. or 50° C. for 2 hours. Then the samples were centrifuged at 12,000 rpm for 10 minutes. Those samples were observed to find possible precipitation, and the samples were analyzed by SEC-HPLC for purity and elution time.

The SEC profile of W3162-1.146.19-Z12 at different conditions was shown in FIG. 14 *a-d*. Neither dilution time nor main peak percentage (92.39% to 92.48%) at high temperature conditions significantly changed, comparing with that at low temperature (92.24%). The SEC profile of W3162-1.154.8-Z35 at different high temperature conditions was shown in FIG. 14 *e-h*. Neither dilution time nor main peak percentage (97.14%-97.17%) significantly changed, compared with at low temperature (96.84%). This set of data indicates that the antibodies were stable in tested high temperature conditions.

2.6 Nonspecific Binding

Both FACS and ELISA assays were used to test whether the antibodies binding to other targets. In FACS assay, different cell lines (Ramos, Raji, MDA-MB-453, BT474, Jurkat, Hut78, A431, A204, CaLu-6, A375, HepG2, BxPC-3, HT29, FaDu, 293F, CHO-K1) were adjusted to $1 \times 10^5$ cells per well. Testing antibodies and Isotype control antibodies were diluted to 10 µg/ml in PBS containing 1% BSA and incubated with cells at 4° C. for 1 hr. The cells were washed twice with 180 µL PBS containing 1% BSA. PE conjugated goat anti-human IgG Fc fragment (Jackson, Catalog number 109-115-098) was diluted to final concentration 5 µg/ml in PBS with 1% BSA, then added to re-suspend cells and incubated at 4° C. in the dark for 30 min. Additional washing steps were performed twice with 180 µL PBS containing 1% BSA followed by centrifugation at 1500 rpm for 4 minutes at 4° C. Finally, the cells were re-suspended in 100 µL PBS containing 1% BSA and fluorescence values were measured by flow cytometry (BD Canto II) and analyzed by FlowJo.

In the ELISA assay, the testing antibodies, isotype control antibodies were tested binding to 10 different target antigens including Factor VIII, FGFR-ECD, PD-1, CTLA-4.ECD, VEGF, HER3.ECD, OX40.ECD, 4-1BB.ECD, CD22.ECD, CD3e.ECD. A 96-well plate was coated with the individual antigens (2 µg/mL) at 4° C. overnight. After 1 hour blocking with 2% BSA in PBS, wash plate 3 times with 300 µL PBST. Testing antibodies, as well as isotype control antibodies were diluted to 10 µg/mL in PBS containing 2% BSA, then were added to the plate and incubated at room temperature for 2 hours. After 3 times washing with 300 µL PBST, HRP-conjugated goat anti-human IgG antibody (1:5000 diluted in 2% BSA) was added to the plate and incubated at room temperature for 1 hours. Finally, the plates were washed six times with 300 µL PBST. The color was developed by dispensing 100 µL of TMB substrate for 12 min, and then stopped by 100 µL of 2M HCl. The absorbance at 450 nM was measured using a microplate spectrophotometer.

Figure 16:
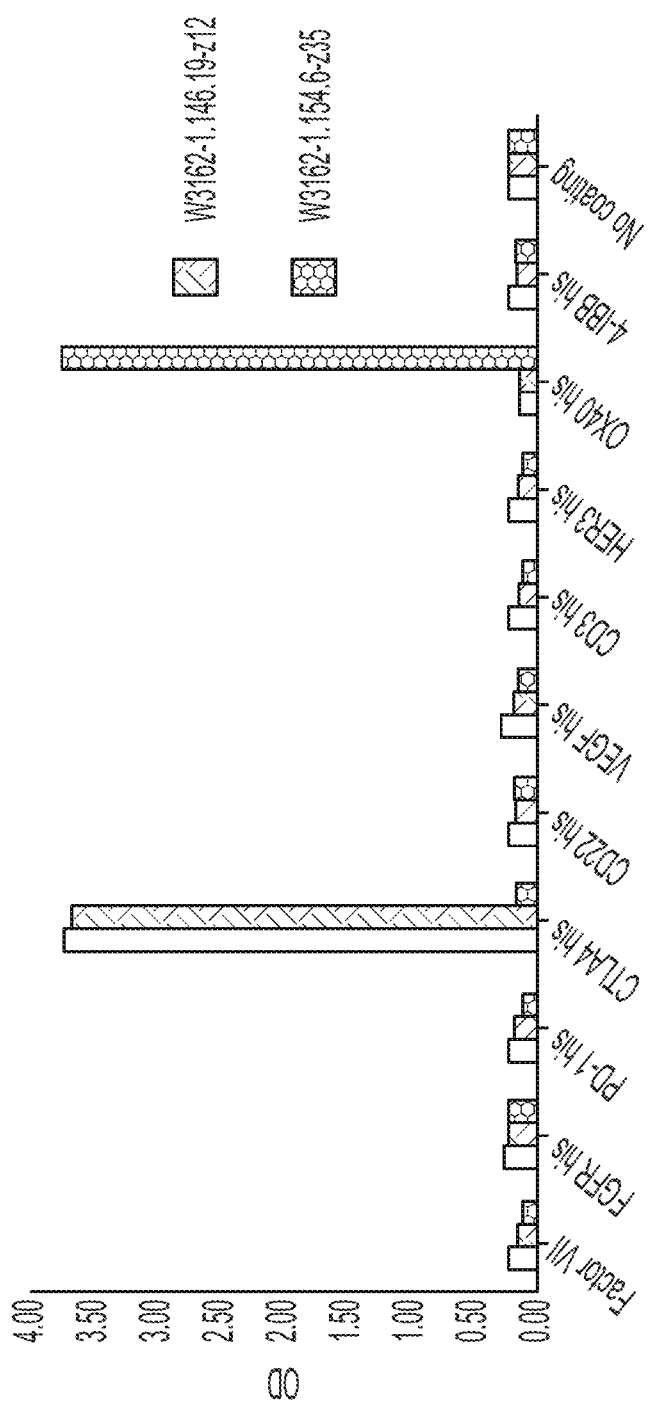
FIG. 16 shows that W3162 antibodies specifically bind to CTLA-4.

In addition to CTLA-4, other irrelevant proteins were used to test whether the antibody W3162-1.146.19-Z12 and W3162-1.154.8-Z35 were able to bind to these antigens. As shown in FIG. 16, among the panel of antigens, only CTLA-4 was detected by the two antibodies. Other antigens did not generate signal in this ELISA assay. On contrast, anti-OX40 antibody did bind to OX40, suggesting this antigen was coated on the plate.

The specificity of the two antibodies were also tested on a panel of different cell lines in FACS assay. The antibodies did not generate detectable signal to any of these cell lines (data not shown).

2.7 In Vivo Efficacy

Due to antibody W3162-1.146.19-Z12 cross-reacts to both human and murine CTLA-4, the anti-tumor efficacy of this antibody was tested in a syngeneic mouse models. Mouse cancer cell line CT26 was used to establish xenograft mouse model to test anti-CTLA-4 antibody W3162-1.146.19-Z12. An anti-murine CTLA-4 antibody purchased from BioXCell was used as a positive control (BioXCell-BE0131). The tumor cells were maintained in vitro as a monolayer culture in RPMI-1640 medium supplemented with 10% fetal bovine serum, 100 U/mL penicillin and 100 µg/mL streptomycin at 37° C. in an atmosphere of 5% $CO_2$. The tumor cells were routinely subcultured twice weekly after detaching the cells by trypsin-EDTA treatment. The cells growing in an exponential growth phase were harvested and counted for tumor inoculation. Female Balb/C mice were purchased from Beijing Vital River Laboratory Animal Co., Ltd. The mice at age 6-8 weeks with weight approximately 18-22 g were used for the study. Each mouse was inoculated subcutaneously at the right axillaries with $1 \times 10^5$ tumor cells in 0.1 mL of PBS mixed with 50 µL matrigel. When the average tumor volume reaches 60-80 $mm^3$, the animals were randomly grouped. The anti-CTLA-4 antibodies and isotype control were used for treatment: intravenously injected into mice twice a week. The tumor size was measured twice weekly by a vernier caliper, and tumor volume was calculated by the formula $a \times b^2 \times \pi / 6$ where a is length and b is width (a>b).

Figure 15:
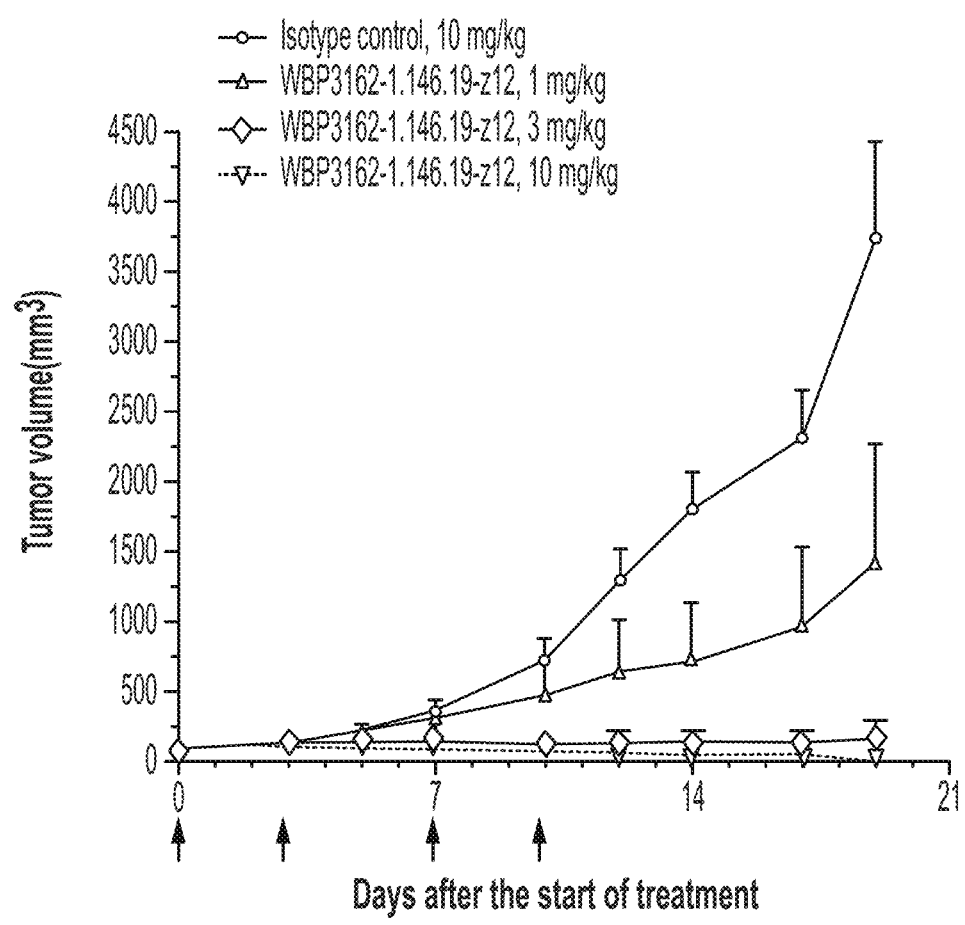
FIG. 15 shows the result of in vivo efficacy of antibody W3162-146.19-z12.

When average tumor volume reached approximately 70 $mm^3$, W3162-1.146.19-Z12 (1 mg/kg, 3 mg/kg, 10 mg/kg) and control antibodies (10 mg/kg) were injected twice a week for two weeks. The animals were monitored for tumor growth and body weight over time. As shown in FIG. 15, W3162-1.146.19-Z12 significantly inhibiting tumor growth in a dose-dependent manner. At 1 mg/kg dose, W3162-1.146.19-Z12 inhibited tumor growth, compared with control group. At 3 mg/kg dose, W3162-1.146.19-Z12 inhibit tumor volume to 160 mm3 at day 19, whereas 10 mg/kg W3162-1.146.19-Z12 induced tumor regression at the end of the study period.

2.8 Epitope Mapping

Alanine scanning was used to identify CTLA-4 epitope of the antibodies. In this experiment, alanine residues on hCTLA4 were mutated to glycine residues, and all other residues were mutated to alanines. For each residue of human CTLA4 extracellular domain (ECD), point amino acid substitutions were made using two sequential PCR steps. A pcDNA3.3-hCTLA4_ECD.His plasmid that encodes ECD of human CTLA4 and a C-terminal His-tag was used as template, and a set of mutagenic primers were used for first step PCR using the QuikChange lightning multi site-directed mutagenesis kit (Agilent technologies, Palo Alto, Calif.). Dpn I endonuclease was used to digest the parental template after mutant strand synthesis reaction. In the second-step PCR, linear DNA expression cassette, composed of a CMV promoter, mutated ECD of CTLA4, a His-tag and a herpes simplex virus thymidine kinase (TK) polyadenylation, was amplified and transiently expressed in HEK293F cells (Life Technologies, Gaithersburg, Md.). In addition, three plasmid vectors were constructed to test the epitope of glycans: pcDNA3.3-hCTLA4_ECD.His (N113 Q), pcDNA3.3-hCTLA4_ECD.His (N145Q), and pcDNA3.3-hCTLA4_ECD.His (N113Q, N145Q). These three muteins were transiently expressed in HEK293F cells (Life Technologies, Gaithersburg, Md.).

In order to test how the mutations affect antibody-binding, a capture ELISA was conducted. Briefly, ipilimumab, W3162-1.146.19-z12 and W3162-1.154.8-z35 (2 µg/mL) monoclonal antibodies were captured by pre-coated with 2 µg/mL goat-anti-human-IgG Fc (Bethyl Laboratories, Montgomery, Tex.) in plates. After interacting with the supernatant that contains quantified CTLA4 muteins, HRP conjugated anti-His antibody (1:5000; Rockland Immunochemicals, Pottstown, Pa.) was added as detection antibody. TMB was used as substance of HRP. Absorbance was normalized according to the average of control mutants. After setting an additional cutoff to the binding fold change (<0.55), the final determined epitope residues were identified.

Figure 17:
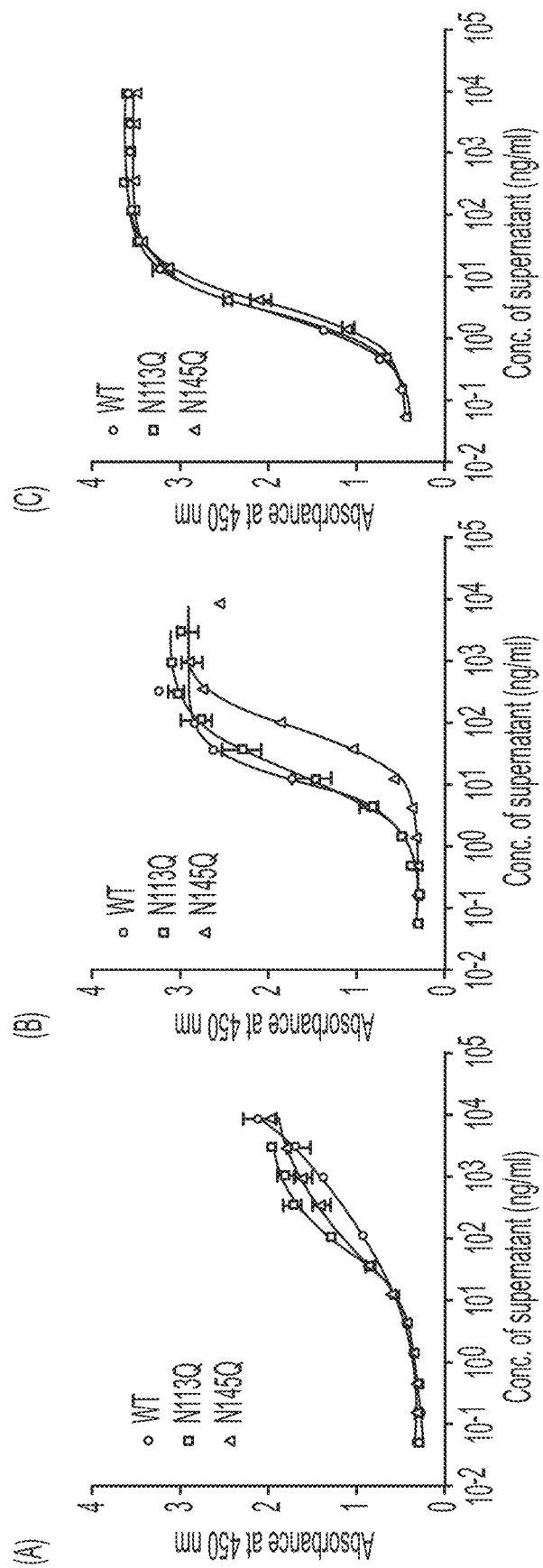
FIG. 17. Binding activity of anti-CTLA4 antibodies with human CTLA-4/CTLA-4 mutants. (A) Ipilimumab, (B) W3162-1.146.19-z12 and (C) W3162-1.154.8-z35 antibodies were captured with pre-coated with 2 µg/ml goat-anti-human-IgG Fc antibody, and then incubated with diluted hCTLA4-His (WT) or its muteins (N113Q and N145Q), then HRP-anti-His antibody was added for detection.

The binding activities of antibodies W3162-1.146.19-z12, W3162-1.154.8-z35 and ipilimumab (W316-BMK1) to human CTLA4 were conducted, all three antibodies were found binding to human CTLA4 (FIG. 17).

The tested point mutations that affect antibody binding to CTLA-4 was shown in Table 11. According to human CTLA4 crystal structures (PDB code 1AH1), some amino acid residues (e.g. Met38, Val40, Tyr60, Val71, Val73, Arg75, Val84, Cys85, Cys129, Ile149) were unlikely to directly contact any antibodies. The observed binding reductions most probably resulted from the instability or even collapse of CTLA4 structure after alanine substitutions. The final determined epitope residues were listed in Table 12 and marked on FIG. 18.

Figure 18:
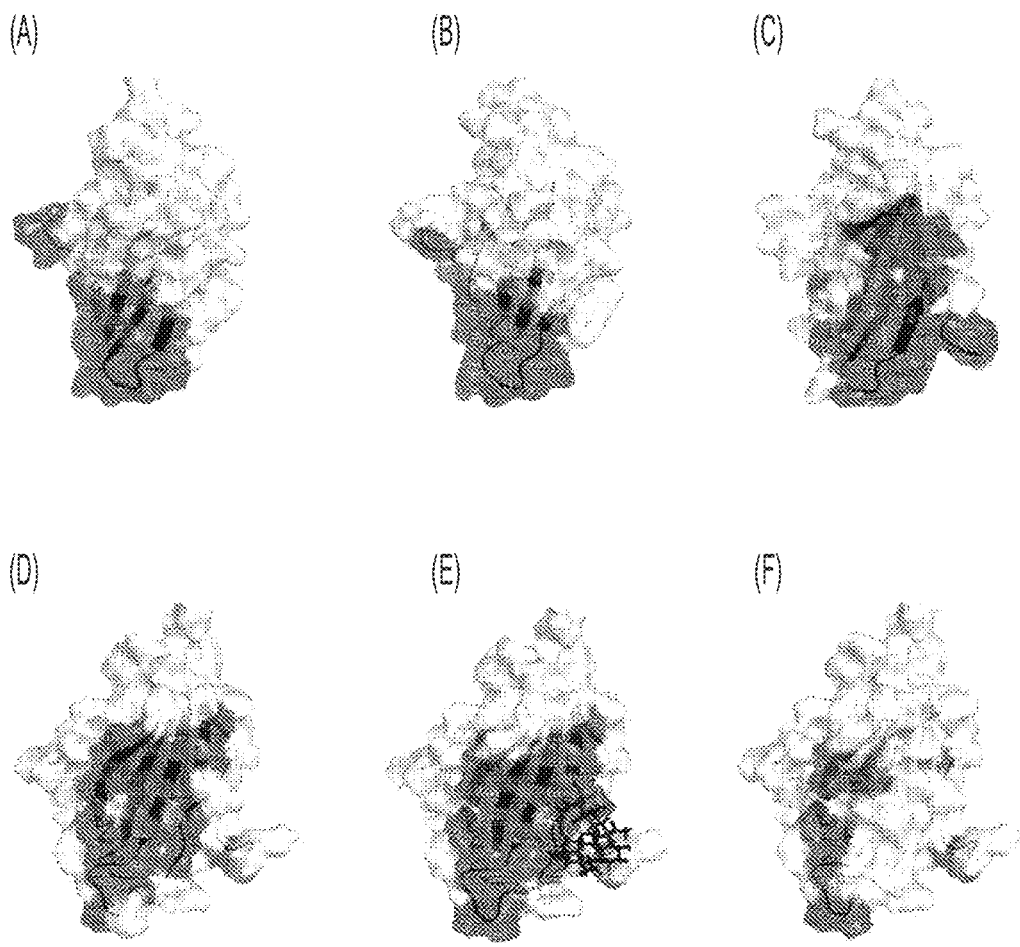
FIG. 18 shows the binding residues or epitopes mapped on human CTLA-4: (A) Binding sites of CD80 (PDB:1I8L), (B) CD86 (PDB:1I85), (C) tremelimumab (PDB: 5GGV), (D) Ipilimumab, (E) W3162-1.146.19-z12 and (F) W3162-1.154.8-z35, respectively. The CTLA-4 structure of 1AH1 was used for D-F to show the structure of glycosylation.

As shown on FIGS. 18D and E, the epitopes of Ipilimumab and W3162-1.146.19-z12 overlap to each other, except a few residues such as N145 and P138. In comparison, W3162-1.154.8-z35 bound to a smaller area of CTLA-4 (FIG. 18 F) than other two antibodies. All the three antibodies bound to ligand binding domain of CTLA-4 (FIGS. 18A and B), which involve the MYPPPY motif (SEQ ID NO: 48).

The overlapped epitopes of Ipilimumab and W3162-1.146.19-z12 did not explain the unique cross-species binding of antibody W3162-1.146.19-z12. As N145 mutation on CTLA-4 only affected W3162-1.146.19-z12 binding to CTLA-4, not affecting other two antibodies, we further looked at the N-glycosylation sites as potential epitopes. The effect of mutations on two glycosylation sites of CTLA4 on antibody-binding activity is shown on FIG. 17. The binding of Ipilimumab or W3162-1.154.8-z35 on mutated CTLA-4 was not significantly changed (FIGS. 17 A and C). In contract, the binding of W3162-1.146.19-z12 on mutated CTLA-4 N145Q significantly reduced whereas this antibody's binding on CTLA-4 with N113Q did not change. This set of data indicates that the glycan (FIG. 18E) on N145 of CTLA-4 could be the epitope of W3162-1.146.19-z12. The N145 residue is conserved in CTLA-4 of cynomoguls monkey and mouse.

The description of the present invention has been made above by the examples. However, it is understood by the skilled in the art that the present invention is not limited to the examples. The invention may be embodied in other specific forms without departing form the spirit or essential characteristics thereof. Scope of the invention is thus indicated by the appended claims rather than by the foregoing description, and all changes that come within the meaning and range of equivalency of the claims are intended to be embraced therein.

TABLE 11

The effect of CTLA4 point mutations on antibody binding

| Ipilimumab | | | | W3162-1.146.19-z12-IgG1K | | | | W3162-1.154.8-z35-IgG1K | | | |
| --- | --- | --- | --- | --- | --- | --- | --- | --- | --- | --- | --- |
| CTLA4 Residue | position | Fold change $^a$ | SD | CTLA4 Residue | position | Fold change $^a$ | SD | CTLA4 Residue | position | Fold change $^a$ | SD |
| P | 136 | 0.191 | 0.00 | G | 146 | 0.166 | 0.00 | P | 136 | 0.155 | 0.00 |
| V | 40 | 0.201 | 0.00 | V | 40 | 0.181 | 0.00 | V | 40 | 0.187 | 0.00 |
| G | 146 | 0.208 | 0.00 | C | 129 | 0.182 | 0.00 | G | 146 | 0.201 | 0.00 |
| C | 129 | 0.210 | 0.00 | M | 38 | 0.182 | 0.00 | C | 129 | 0.211 | 0.00 |
| C | 85 | 0.229 | 0.00 | I | 149 | 0.183 | 0.00 | C | 85 | 0.218 | 0.00 |
| V | 84 | 0.233 | 0.01 | V | 81 | 0.191 | 0.01 | V | 84 | 0.232 | 0.00 |
| Y | 60 | 0.236 | 0.04 | N* | 145 | 0.196 | 0.00 | M | 38 | 0.238 | 0.00 |
| M | 134 | 0.240 | 0.01 | Q | 76 | 0.200 | 0.00 | Y | 60 | 0.240 | 0.07 |
| I | 149 | 0.244 | 0.01 | V | 84 | 0.201 | 0.00 | R | 75 | 0.298 | 0.00 |
| M | 38 | 0.253 | 0.02 | Y | 60 | 0.223 | 0.05 | I | 149 | 0.319 | 0.00 |
| V | 81 | 0.268 | 0.03 | P | 136 | 0.231 | 0.00 | P | 138 | 0.339 | 0.00 |
| R | 75 | 0.273 | 0.00 | M | 134 | 0.254 | 0.00 | V | 71 | 0.347 | 0.10 |
| I | 143 | 0.278 | 0.00 | I | 128 | 0.256 | 0.00 | K | 65 | 0.351 | 0.00 |
| I | 128 | 0.286 | 0.00 | C | 85 | 0.256 | 0.03 | T | 88 | 0.433 | 0.02 |
| V | 71 | 0.335 | 0.08 | I | 143 | 0.264 | 0.00 | M | 134 | 0.455 | 0.00 |
| K | 130 | 0.364 | 0.00 | R | 75 | 0.278 | 0.00 | E | 83 | 0.479 | 0.00 |
| G | 142 | 0.369 | 0.01 | V | 73 | 0.338 | 0.01 | V | 73 | 0.498 | 0.01 |
| G | 144 | 0.375 | 0.00 | V | 71 | 0.343 | 0.06 | R | 70 | 0.515 | 0.04 |
| T | 88 | 0.377 | 0.06 | K | 130 | 0.348 | 0.00 | A | 66 | 0.519 | 0.02 |
| R | 70 | 0.378 | 0.10 | A | 66 | 0.395 | 0.02 | L | 74 | 0.520 | 0.00 |
| V | 73 | 0.380 | 0.00 | L | 74 | 0.398 | 0.00 | P | 137 | 0.534 | 0.00 |
| A | 66 | 0.395 | 0.03 | L | 126 | 0.398 | 0.02 | G | 64 | 0.543 | 0.10 |
| E | 83 | 0.396 | 0.02 | E | 83 | 0.405 | 0.01 | H | 39 | 0.549 | 0.01 |
| A | 86 | 0.401 | 0.03 | T | 88 | 0.423 | 0.06 | | | | |
| P | 137 | 0.407 | 0.00 | P | 137 | 0.425 | 0.00 | | | | |

TABLE 11-continued

The effect of CTLA4 point mutations on antibody binding

| Ipilimumab | | | | W3162-1.146.19-z12-IgG1K | | | | W3162-1.154.8-z35-IgG1K | | | |
| --- | --- | --- | --- | --- | --- | --- | --- | --- | --- | --- | --- |
| CTLA4 Residue | position | Fold change [a] | SD | CTLA4 Residue | position | Fold change [a] | SD | CTLA4 Residue | position | Fold change [a] | SD |
| L | 74  | 0.410 | 0.00 | Y | 139 | 0.431 | 0.00 | | | | |
| L | 126 | 0.412 | 0.01 | T | 82  | 0.436 | 0.00 | | | | |
| H | 39  | 0.420 | 0.01 | P | 138 | 0.445 | 0.00 | | | | |
| Y | 139 | 0.434 | 0.00 | E | 132 | 0.457 | 0.01 | | | | |
| T | 82  | 0.450 | 0.01 | G | 144 | 0.478 | 0.00 | | | | |
| E | 132 | 0.470 | 0.04 | T | 147 | 0.486 | 0.03 | | | | |
| M | 90  | 0.479 | 0.02 | L | 141 | 0.486 | 0.00 | | | | |
| T | 147 | 0.508 | 0.03 | M | 90  | 0.492 | 0.00 | | | | |
| Y | 127 | 0.508 | 0.01 | Q | 148 | 0.500 | 0.02 | | | | |
| Q | 80  | 0.517 | 0.02 | V | 131 | 0.504 | 0.02 | | | | |
| L | 141 | 0.518 | 0.03 | R | 70  | 0.507 | 0.08 | | | | |
| E | 68  | 0.529 | 0.00 | Y | 89  | 0.512 | 0.05 | | | | |
| Q | 148 | 0.532 | 0.04 | Y | 127 | 0.529 | 0.02 | | | | |
| G | 125 | 0.537 | 0.02 | H | 39  | 0.529 | 0.00 | | | | |
| Q | 76  | 0.545 | 0.00 | T | 72  | 0.541 | 0.01 | | | | |
| G | 92  | 0.548 | 0.00 | G | 142 | 0.543 | 0.02 | | | | |
|   |     |       |      | C | 103 | 0.544 | 0.03 | | | | |

[a] Fold change in binding is relative to the binding of several silent alanine substitutions.

TABLE 12

Identified epitopes of three antibodies

| Ipilimumab | | | W3162-1.146.19-z12-IgG1K | | | W3162-1.154.8-z35-IgG1K | | |
| --- | --- | --- | --- | --- | --- | --- | --- | --- |
| CTLA4 Residue | Position | Location | CTLA4 Residue | Position | Location | CTLA4 Residue | Position | Location |
| H | 39  | A        | H | 39  | A        | H | 39  | A |
| A | 66  | B C loop | A | 66  | B C loop | G | 64  | B C loop |
| E | 68  | C        | R | 70  | C        | K | 65  | B C loop |
| R | 70  | C        | T | 72  | C        | A | 66  | B C loop |
| L | 74  | C        | L | 74  | C        | R | 70  | C |
| Q | 76  | C        | Q | 76  | C        | L | 74  | C |
| Q | 80  | C'       | V | 81  | C'       | E | 83  | C' |
| V | 81  | C'       | T | 82  | C'       | T | 88  | C' |
| T | 82  | C'       | E | 83  | C'       | M | 134 | F |
| E | 83  | C'       | T | 88  | C'       | P | 136 | FG loop |
| A | 86  | C'       | M | 90  | C' C" loop | P | 137 | FG loop |
| T | 88  | C'       | G | 92  | C"       | P | 138 | FG loop |
| M | 90  | C' C" loop | L | 126 | F      | G | 146 | G |
| G | 92  | C"       | I | 128 | F        |   |     |   |
| G | 125 | F        | K | 130 | F        |   |     |   |
| L | 126 | F        | E | 132 | F        |   |     |   |
| I | 128 | F        | M | 134 | F        |   |     |   |
| K | 130 | F        | P | 136 | FG loop  |   |     |   |
| E | 132 | F        | P | 137 | FG loop  |   |     |   |
| M | 134 | F        | P | 138 | FG loop  |   |     |   |
| P | 136 | FG loop  | Y | 139 | FG loop  |   |     |   |
| P | 137 | FG loop  | L | 141 | G        |   |     |   |
| Y | 139 | FG loop  | G | 142 | G        |   |     |   |
| L | 141 | G        | I | 143 | G        |   |     |   |
| G | 142 | G        | G | 144 | G        |   |     |   |
| I | 143 | G        | N | 145 | G        |   |     |   |
| G | 144 | G        | G | 146 | G        |   |     |   |
| G | 146 | G        | Q | 148 | G        |   |     |   |
| Q | 148 | G        |   |     |          |   |     |   |

The invention claimed is:

1. An immunoglobulin comprising:
   a) a variable region of a heavy chain having an amino acid sequence that is at least 90% identical to SEQ ID NO: 7; and
   b) a variable region of a light chain having an amino acid sequence that is at least 90% identical to SEQ ID NO: 14,
   wherein the immunoglobulin comprises
   a light chain variable region comprising a light chain complementary-determining region 1 (LCDR1) defined by SEQ ID NO: 41, LCDR2 defined by defined by SEQ ID NO: 32, and LCDR3 defined by SEQ ID NO: 22, and
   a heavy chain variable region comprising a heavy chain complementary determining region 1 (HCDR1) defined by SEQ ID NO: 36, HCDR2 defined by defined by SEQ ID NO: 28, and HCDR3 defined by SEQ ID NO: 18.

2. The immunoglobulin according to claim 1, wherein the immunoglobulin is a chimeric, humanized, or rat antibody.

3. A pharmaceutical composition comprising the immunoglobulin according to claim 1, and one or more of a pharmaceutically acceptable excipient, a diluent and a carrier.

4. An immunoconjugate comprising the immunoglobulin according to claim 1, linked to a therapeutic agent.

* * * * *